United States Patent [19]

Inukai et al.

[11] Patent Number: 5,068,239
[45] Date of Patent: Nov. 26, 1991

[54] TETRAZOLEACETIC ACID DERIVATIVES AND USE FOR ALDOSE REDUCTASE INHIBITORY ACTIVITY

[75] Inventors: Sinji Inukai, Hatano; Mitsuzi Agata, Kanagawa; Manami Umezawa, Morinosato; Yoshihiro Horio, Hatano; Yasuhiro Ootake, Minami-ashigara; Shohei Sawaki, Kanagawa; Masayoshi Goto, Isehara, all of Japan

[73] Assignee: Wakamoto Pharmaceutical Co., Ltd., Tokyo, Japan

[21] Appl. No.: 588,057

[22] Filed: Sep. 24, 1990

[30] Foreign Application Priority Data

Oct. 3, 1989 [JP] Japan .................................. 1-257086

[51] Int. Cl.$^5$ .................... C07D 257/04; A61K 31/41
[52] U.S. Cl. ..................................... 514/381; 548/253
[58] Field of Search ......................... 514/381; 548/253

[56] References Cited

U.S. PATENT DOCUMENTS 4,886,885 12/1989 Baker et al. ........................ 514/381

OTHER PUBLICATIONS

Robert T. Buckler et al., Synthesis and Antiinflammatory Activity of some Aryltetrazolylalkanoic Acids, *J. Med. Chem.* 13:725-729 (1970).
C. R. Jacobson and E. D. Amstutz, Studies in Tetrazole Chemistry, IV. Tetrazolylacetic Acids and Esters, *J. Org. Chem.* 21:311-315 (1955).
R. Rapp and J. Howard, Tetrazolylacetic acids, *Can. J. Chem.* 47:813-819 (1969).
Fred Einberg, Alkylation of 5-Substituted Tetrazoles with α-Chlorocarbonyl Compounds, *J. Org. Chem.* 35:3978-3980 (1970).
L'ubomir Janda et al., Semisynthetic Cephalosporines, the Synthesis of Some Substituted Tetrazolylacetic Acids, *Coll. Czech. Chem. Commun.* 49:1505-1514 (1984).
L'ubomir Janda et al., Semisynthetic Cephalosporines, Synthesis of Some Substituted Tetrazolyl Acetic and Propionic Acids, *Coll. Czech. Chem. Commun.* 49:1699-1713 (1984).
L. Janda and Z. Voticky, Synthesis of Some Substituted Tetrazolylacetic Acids, *Chem. Papers* 43 (1):63-71, (1989).
A. K. Sorensen et al., Syntheses of Some New Tetrazolylacetic Acids and the Corresponding 3-Substituted Propionic Acids, *Acta Chem. Scand.* 26:541-548 (1972).
G. Szeimies et al., Synthese und Thermisches Verhalten Ciniger 3-Aryl-3-Azido-Aziridin-2-Carbonsaure--Ethylester, *Chem. Ber.* 110:2922-2938 (1977).
V. S. Poplavskii et al., Tetrazoles *Zhurnal organicheskoi khimii*, 1982, XVIII, No. 9, 1981-1985.

Primary Examiner—David B. Springer
Attorney, Agent, or Firm—Seed and Berry

[57] ABSTRACT

A tetrazoleacetic acid derivative represented by the following general formula (I):

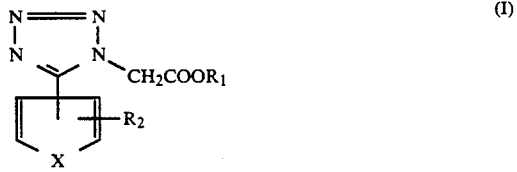

[in Formula (I), $R_1$ represents a hydrogen atom or an alkyl group; $R_2$ represents a hydrogen atom, an alkyl group, an aralkyl group, a halogen atom, a haloalkyl group, a hydroxyl group, an alkoxy group, an alkoxyalkyl group, an amino group, an aryl group, an alkyl or aryl thio group, an alkyl or aryl carbonylamino group, an alkyl or aryl sulfonylamino group, an alkyl or aryl aminosulfonyl group, an alkyl or aryl sulfonyl group or an alkyl or aryl sulfinyl group; and X represents —O— or —S—] except for [5-(2-thienyl)tetrazol-1-yl] acetic acid, [5-(2-furyl)tetrazol-1-yl] acetic acid and ethyl esters thereof, or a salt thereof shows excellent aldose reductase inhibitory activity, has low toxicity to organisms and is quite effective as an essential component of a preventive medicine and/or remedy for diabetic complications.

20 Claims, No Drawings

TETRAZOLEACETIC ACID DERIVATIVES AND USE FOR ALDOSE REDUCTASE INHIBITORY ACTIVITY

BACKGROUND OF THE INVENTION

1. Field of the Invention

The present invention relates to a compound having an aldose reductase inhibitory activity and more specifically to a tetrazoleacetic acid derivative and an aldose reductase inhibitor which comprises the tetrazoleacetic acid derivative as an effective component and which is effective as a preventive medicine and/or remedy for diabetic complications as well as a method for alleviating or reducing diabetic complications.

2. Prior Art

It has been known that aldose reductase inhibitors are effective for prevention and/or treatment of diabetic copmplications. This is detailed in the article of Dr. Tsuyoshi TANIMOTO [Division of Biological Chemistry and Reference Standards, National Institute of Hygienic Sciences] (see Farumashia, 1988,24, No. 5, pp. 459-463). This article discloses the chemical structures and 50% inhibitory concentrations ($IC_{50}$) of representative aldose reductase inhibitors such as Alrestatin, Tolrestat, 4-Isopropyl-BFOC, Sorbinil, M-79175, Alconil, ADN-138, Epalrestat, CT-112 and Statil.

The inventors of this invention already conducted screening of novel aldose reductase inhibitors, found that compounds represented by the following general formula (III):

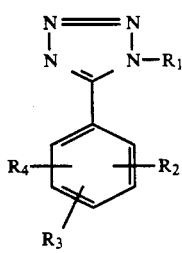

[in Formula (III), $R_1$ represents a hydrogen atom or a group: —A—$COOR_5$ (wherein A represents an alkylene group having 1–4 carbon atoms and $R_5$ represents a hydrogen atom or a lower alkyl group) and $R_2$, $R_3$ and $R_4$ may be the same or different and each represents a hydrogen atom, a halogen atom, an alkyl group, an alkoxy group, a phenyl group, a phenoxy group, a nitro group, a residue represented by the formula: NHCO-$COOR_6$ (wherein $R_6$ represents a hydrogen atom or a lower alkyl group) or a residue represented by the following formula:

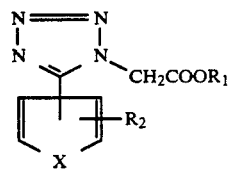

wherein A and $R_5$ are the same as those defined above)] have very high aldose reductase inhibitory activity and already filed a patent application (Japanese Patent Application Serial No. Hei 1-70520).

Among these chemical substances according to the present invention, [5-(2-thienyl)tetrazol-1-yl] acetic acid and ethyl ester thereof as well as [5-(2-furyl)tetrazol-1-yl] acetic acid and ethyl ester thereof are reported in an article of A. K. Zorenzen, Acta Chem. Scand., 1972, 26, p. 541. However, this article only discloses a method for preparing these substances, but there is no disclosure about the biological activity thereof.

SUMMARY OF THE INVENTION

Accordingly, an object of the present invention is generally to provide a compound which shows excellent aldose reductase inhibitory activity, has low toxicity to organisms and is quite effective as a preventive medicine and/or remedy for diabetic complications and more specifically to provide a tetrazoleacetic acid derivative.

Another object of the present invention is to provide an aldose reductase inhibitor which comprises the tetrazoleacetic acid derivative as an effective component and which is effective as a preventive medicine and/or remedy for diabetic complications.

A further object of the present invention is to provide a method for alleviating or reducing symptoms related to diabetic complications.

According to an aspect of the present invention, there is provided a novel tetrazoleacetic acid derivative represented by the following general formula (I):

[in Formula (I), $R_1$ represents a hydrogen atom or an alkyl group; $R_2$ represents a hydrogen atom, an alkyl group, an aralkyl group, a halogen atom, a haloalkyl group, a hydroxyl group, an alkoxy group, an alkoxyalkyl group, an amino group, an aryl group, an alkyl or aryl thio group, an alkyl or aryl carbonylamino group, an alkyl or aryl sulfonylamino group, an alkyl or aryl aminosulfonyl group, an alkyl or aryl sulfonyl group or an alkyl or aryl sulfinyl group; and X represents —O— or —S—] except for [5-(2-thienyl)tetrazol-1-yl] acetic acid, [5-(2-furyl)tetrazol-1-yl] acetic acid and ethyl esters thereof, or a salt thereof.

According to another aspect of the present invention, there is provided an aldose reductase inhibitor which comprises a tetrazoleacetic acid derivative represented by the following general formula (II):

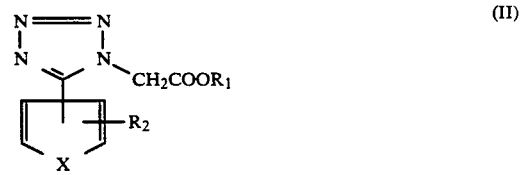

[in Formula (II), $R_1$ represents a hydrogen atom or an alkyl group; $R_2$ represents a hydrogen atom, an alkyl group, an aralkyl group, a halogen atom, a haloalkyl group, a hydroxyl group, an alkoxy group, an alkoxyalkyl group, an amino group, an aryl group, an alkyl or aryl thio group, an alkyl or aryl carbonylamino group, an alkyl or aryl sulfonylamino group, an alkyl or aryl aminosulfonyl group, an alkyl or aryl sulfonyl group or an alkyl or aryl sulfinyl group; and X represents —O— or —S—] or a salt thereof and a pharmaceutical acceptable carrier.

According to a further aspect of the present invention, there is provided a method for alleviating or reducing diabetic complications wherein a tetrazoleacetic acid derivative represented by the following general formula (II):

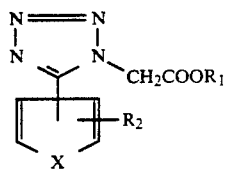

(II)

[in Formula (II), $R_1$ represents a hydrogen atom or an alkyl group; $R_2$ represents a hydrogen atom, an alkyl group, an aralkyl group, a halogen atom, a haloalkyl group, a hydroxyl group, an alkoxy group, an alkoxyalkyl group, an amino group, an aryl group, an alkyl or aryl thio group, an alkyl or aryl carbonylamino group, an alkyl or aryl sulfonylamino group, an alkyl or aryl aminosulfonyl group, an alkyl or aryl sulfonyl group or an alkyl or aryl sulfinyl group; and X represents —O— or —S—] or a salt thereof is used.

DETAILED EXPLANATION OF THE INVENTION

The tetrazoleacetic acid derivatives and the aldose reductase inhibitor as well as the method for alleviating diabetic complications according to the present invention will hereunder be explained in more detail.

First, each substituent in Formulae (I) and (II) will be explained in detail.

The alkyl group represented by $R_1$ or $R_2$ is, for instance, methyl, ethyl, propyl, isopropyl, butyl, isobutyl or t-butyl group; the aralkyl group includes, for instance, phenylpropyl and benzyl group; examples of the alkoxy groups are methoxy, ethoxy, propoxy, isopropoxy, butoxy, isobutoxy and t-butoxy groups; examples of the alkoxyalkyl groups are methoxymethyl and butoxymethyl groups; the haloalkyl groups are, for instance, mono-, di- or tri-haloalkyl groups such as chloromethyl, bromomethyl, fluoromethyl and chlorobutyl groups; the alkyl or aryl thio groups are, for instance, methylthio, ethylthio, butylthio and phenylthio groups; the alkylaminosulfonyl groups include, for instance, mono- or di-alkylaminosulfonyl groups such as methylaminosulfonyl, ethylaminosulfonyl, propylaminosulfonyl and butylaminosulfonyl groups; the alkyl or aryl sulfonylamino groups are, for instance, methylsulfonylamino, ethylsulfonylamino, butylsulfonylamino and phenylsulfonylamino groups; examples of the alkyl or aryl carbonylamino groups are methylcarbonylamino, ethylcarbonylamino, propylcarbonylamino and phenethylcarbonylamino groups; examples of the alkyl or aryl sulfonyl groups are methylsulfonyl, ethylsulfonyl, butylsulfonyl and piperidinosulfonyl groups; and examples of the alkylsulfinyl groups are methylsulfinyl, ethylsulfinyl and butylsulfinyl groups. These substituents may be present on any position on the furan or thiophene ring.

In addition, salts of the foregoing compounds represented by Formulae (I) and (II) wherein $R_1$ is a hydrogen atom are pharmaceutically acceptable ones and typical examples thereof include inorganic salts such as alkali metal salts (for instance, sodium salts and potassium salts), alkaline earth metal salts (for instance, calcium salts and magnesium salts) and ammonium salts; and organic salts such as organic amine salts (for instance, triethylamine salts, pyridine salts and ethanolamine salts) and salts with basic amino acids, for instance, arginine.

The aldose reductase inhibitors according to the present invention comprises, as an essential component, at least one compound represented by the foregoing general formula (II) and are effective as preventive medicines and/or remedies for diabetic complications. It has been known that the term "diabetic complications" means a variety of pathema such as peripheral disorder, retinopathy, nephrosis, cataract and keratopathy. These diseases or disorders are triggered by hyperglycemia resulted from the diabetic disease, that the production of sorbitol in the polyol metabolic pathway is correspondingly abnormally accelerated and that, as a result, a large amount of sorbitol is accumulated within cells. This leads to the onset of these diseases.

The aldose reductase inhibitors of the present invention can suppress the sorbitol-production through strong inhibition of the activity of the aldose reductase which catalyzes the sorbitol-production in the foregoing polyol metabolic pathway and thus show excellent preventive and/or treating effects for these various diabetic complications.

The dose of the compounds of Formulae (I) and (II) is appropriately determined depending on the conditions or symptoms of patients to be treated, but in general ranges from 1 to 1,000 mg per day for adult which is administered at one time or over several times. The compounds may be administered through any route for medication such as oral administration, subcutaneous injection, intravenous injection and local administration.

The aldose reductase inhibitors of the present invention may usually comprise, in addition to the foregoing compounds as the essential components, pharmaceutically acceptable carriers, vehicles and other additives. The inhibitors of the invention may be used in any dosage form such as tablets, powder, fine particles, granules, capsules, pills, liquid preparations, solutions and suspension for injection and eye drops.

Then methods for preparing the compounds (I) as the essential components, conditions therefor or the like will be detailed below with reference to the following reaction schemes.

Reaction Scheme 1: Preparation of Tetrazole Ring

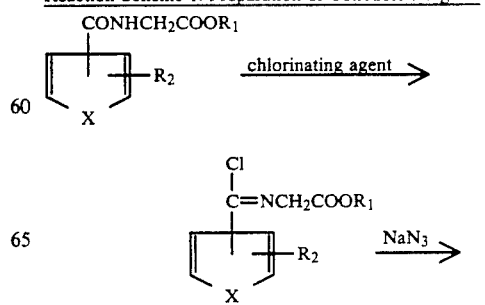

-continued

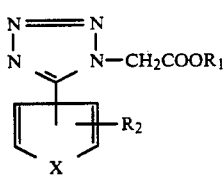

Reaction Scheme 2: Conversion of $R_1$ Into Hydrogen Atom

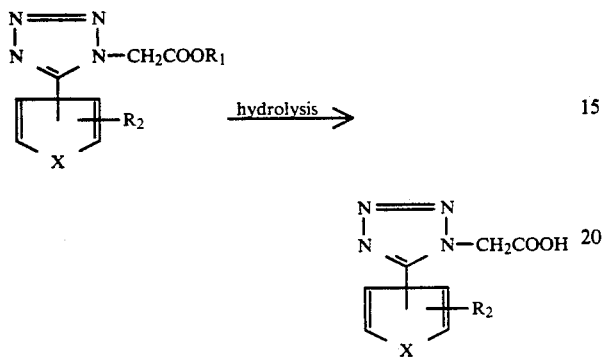

The reaction scheme 1 shows the tetrazole ring formation reaction in which N-aryloylaminoalkyl carboxylate is reacted with a chlorinating agent such as phosphorus pentoxide, thionyl chloride or thionyl chloride/N,N dimethylformamide to obtain a corresponding imidoyl chloride compound and then the product is reacted with sodium azide to obtain an intended compound of Formula (I). The reaction for obtaining the imidoyl chloride can be carried out in an organic solvent such as benzene, toluene or methylene chloride. In general, the reaction is preferably performed at a temperature of not more than room temperature. In the subsequent cyclization reaction, it is preferred to use sodium azide in an amount of 2 to 6 times that of the imidoyl chloride as an intermediate. The cyclization reaction is in general performed at room temperature in N,N-dimethylformamide.

The reaction scheme 2 means that the compounds of Formula (I) in which $R_1$ is a hydrogen atom may be prepared by hydrolysis of the carboxylic acid ester obtained in the reaction scheme 1. The hydrolysis can be performed in the presence of a base such as sodium hydroxide or potassium hydroxide or an acid such as hydrochloric acid, sulfuric acid, acetic acid or trifluoroacetic acid.

The compounds of Formula (I) Prepared according to the foregoing method are separated and purified by a chemical operation commonly employed such as extraction, recrystallization and/or column chromatography and the products thus separated and purified are used as essential components for the aldose reductase inhibitors of the present invention.

The present invention will hereinafter described in more detail with reference to the following non-limitative working Examples and the effects practically achieved by the present invention will also be discussed in detail with reference to Test Examples.

EXAMPLE 1

(1-1) preparation of methyl [5-(2-thienyl)tetrazol-1-yl] acetate

To a solution of 1 g (5.02 mM) of N-(2-thenoyl)glycine methyl ester in 15 ml of anhydrous methylene chloride, there was slowly added 1.5 g (7.2 mM) of phosphorus pentoxide at room temperature with stirring, the resulting mixture was stirred for additional 30 minutes and the reaction solution was concentrated at 40° C. under reduced pressure. The resulting residue was dissolved in 5 ml of N,N-dimethylformamide. The solution was dropwise added to a suspension of 1.6 g (24.6 mM) of sodium azide in 3 ml of N,N-dimethylformamide at room temperature over 30 minutes with stirring. After the dropwise addition and agitation for additional 30 minutes at room temperature, the mixture was poured into ice-water and extracted with ethyl acetate. The organic phase obtained was washed with water, dried over anhydrous sodium sulfate and then concentrated under reduced pressure. The resultant residue was subjected to silica gel column chromatography (eluent: ethyl acetate/benzene=1/20) for separation and purification to thus give 0.59 g (yield 52.4%) of methyl [5-(2-thienyl)tetrazol-1-yl] acetate.

M.P.=73-74° C.

N.M.R. (CDCl$_3$) δppm: 3.84 (s, 3H); 5.34 (s, 2H); 7.24 (dd, 1H, J=5.20, 3.60 Hz); 7.58 (dd, 1H, J=3.60, 1.20 Hz); 7.65 (dd, 1H, J=5.20, 1.20 Hz).

I.R. νKBr (cm$^{-1}$): 3400, 1730, 1650, 1540, 1370, 1230.

Mass: m/z 224 [M+]

The following compounds were prepared in the same manner used in Example (1-1)

(1-2) methyl [5-(3-methyl-2-thienyl)tetrazol-1-yl] acetate (yield 51.1%)

Starting material: N-(3-methyl-2-thenoyl)glycine methyl ester

N.M.R. (CDCl$_3$) δppm: 2.43 (s, 3H); 3.80 (s, 3H); 5.25 (s, 2H); 7.07 (d, 1H, J=5.0 Hz); 7.52 (d, 1H, J=5.0 Hz).

I.R. νNaCl (cm$^{-1}$): 3100, 2950, 1760, 1440, 1220, 1000.

Mass: m/z 238 [M+]

(1-3) methyl [5-(4-methyl-2-thienyl)tetrazol-1-yl] acetate (yield 48.8%)

Starting material: N-(4-methyl-2-thenoyl)glycine methyl ester

N.M.R. (CDCl$_3$) δpm: 2.34 (s, 3H); 3.83 (s, 3H); 5.33 (s, 2H); 7.22 (d, 1H, J=1.2 Hz); 7.41 (d, 1H, J=1.2 Hz).

I.R. νNaCl (cm$^{-1}$): 3090. 2950, 1740, 1580, 1440, 1240.

Mass: m/z 238 [M+]

(1-4) methyl [5-(5-methyl-2-thienyl)tetrazol-1-yl] acetate (yield 50.1%)

Starting material: N (5-methyl-2-thenoyl)glycine methyl ester

M.P.=88-89° C.

N.M.R. (CDCl$_3$) δppm: 2.57 (s, 3H); 3.83 (s, 3H); 5.32 (s, 2H); 6.87~6.89 (m, 1H); 7.36~7.39 (m, 1H).

I.R. νKBr (cm$^{-1}$): 3440, 1750, 1580, 1510, 1430, 1260, 1230, 1100.

Mass: m/z 238 [M+]

(1-5) methyl [5-(3-thienyl)tetrazol-1-yl] acetate (yield 52%)

Starting material: N-(3-thenoyl)glycine methyl ester

M.P.=106-107° C.

N.M.R. (CDCl$_3$) δppm: 3.84 (s, 3H); 5.27 (s, 2H); 7.48 (dd, 1H, J=5.01, 1.20 Hz); 7.56 (dd, 1H, J=5.01, 2.80 Hz); 8.25 (dd, 1H, J=2.80, 1.20 Hz)

I.R. νKBr (cm$^{-1}$): 3100, 1760, 1580, 1440, 1360, 1230.

Mass: m/z 224 [M+]

(1-6) methyl [5-(2-furyl)tetrazol-1-yl] acetate (yield 24%)

Starting material: N-(2-furoyl)glycine methyl ester
N.M.R. (CDCl$_3$) δppm: 3.79 (s, 3H); 5.49 (s, 2H); 6.66 (dd, 1H, J=3.60, 2.01 Hz); 7.36 (dd, 1H, J=3.60, 0.80 Hz); 7.64 (dd, 1H, J=2.01, 0.80 Hz)
I.R. νNaCl (cm$^{-1}$): 3120, 3000, 2950, 1750, 1620, 1520, 1440, 1220, 1010.
Mass: m/z 208 [M+]

(1-7) methyl [5-(3-furyl)tetrazol-1-yl] acetate (yield 30%)

Starting material: N-(3-furoyl)glycine methyl ester
N.M.R. (CDCl$_3$) δppm: 3.84 (s, 3H); 5.24 (s, 2H); 6.81 (bs, 1H); 7.63 (bs, 1H); 7.96 (bs, 1H)
I.R. νNaCl (cm$^{-1}$): 3140, 2950, 1750, 1440, 1220.
Mass: m/z 208 [M+]

(1-8) methyl [5-(5-ethyl-2-thienyl)tetrazol-1-yl] acetate (yield 44.0%)

Starting material: N-(5-ethyl-2-thenoyl)glycine methyl ester
M.P.=45-46° C.
N.M.R. (CDCl$_3$) δppm: 1.36 (t, 3H, J=7.70 Hz); 2.91 (dq, 2H, J=7.70, 0.80 Hz); 3.83 (s, 3H); 5.32 (s, 2H); 6.91 (dt, 1H, J=3.60, 0.80 Hz); 7.40 (d, 1H, J=3.60 Hz)
I.R. νKBr (cm$^{-1}$): 2960, 1760, 1580, 1510, 1430, 1270, 1220, 1100, 1000, 820.
Mass: m/z 252 [M+]

(1-9) methyl [5-(5-benzyl-2-thienyl)tetrazol-1-yl] acetate (yield 38.0%)

Starting material: N-(5-benzyl-2-thenoyl)glycine methyl ester
M.P.=71-72° C.
N.M.R. (CDCl$_3$) δppm: 3.80 (s, 3H); 4.20 (s, 2H); 5.29 (s, 2H); 6.91 (dt, 1H, J=4.01, 1.20 Hz); 7.23~7.38 (m, 5H); 7.39 (d, 1H, J=4.01 Hz)
I.R. νKBr (cm$^{-1}$): 3000, 1740, 1580, 1510, 1460, 1420, 1380, 1270, 1240, 800.
Mass: m/z 314 [M+]

(1-10) methyl [5-(5-methylthio-2-thienyl)tetrazol-1-yl] acetate (yield 66%)

Starting material: N-(5-methylthio-2-thenoyl)glycine methyl ester
M.P.=64-65° C.
N.M.R. (CDCl$_3$) δppm: 2.60 (s, 3H); 3.84 (s, 3H); 5.31 (s, 2H); 7.07 (d, 1H, J=4.00 Hz); 7.45 (d, 1H, J=4.00 Hz)
I.R. νKBr (cm$^{-1}$): 3470, 1750, 1580, 1480, 1440, 1410, 1360, 1260, 1220, 1100, 990, 790.
Mass: m/z 270 [M+]

(1-11) methyl [5-(5-bromo-2-thienyl)tetrazol-1-yl] acetate (yield 55.0%)

Starting material: N-(5-bromo-2-thenoyl)glycine methyl ester
M.P.=45-46° C.
N.M.R. CDCl$_3$) δppm: 3.84 (s, 3H); 5.30 (s, 2H); 7.19 (d, 1H, J=4.90 Hz); 7.30 (d, 1H, J=4.90 Hz)
I.R. νKBr (cm$^{-1}$): 3450, 1740, 1580, 1490, 1440, 1400, 1270, 1240, 1100, 980, 800.
Mass: m/z 303 [M+]

(1-12) methyl [5-(2-bromo-3-thienyl)tetrazol-1-yl] acetate (yield 49.7%)

Starting material: N-(2-bromo-3-thenoyl)glycine methyl ester
N.M.R. CDCl$_3$) δppm: 2.58 (s, 3H); 3.80 (s, 3H); 5.12 (s, 2H, 6.99 (d, 1H, J=5.20 Hz); 7.27 (d, 1H, J=5.20 Hz)
I.R. νNaCl (cm$^{-1}$): 2950, 1750, 1580, 1500, 1440, 1260, 1220.
Mass: m/z 238 [M+]

(1-13) methyl [5-(5-bromomethyl-2-thienyl)tetrazol-1-yl] acetate (yield 50.9%)

Starting material: N-(5-bromomethyl-2-thenoyl)glycine methyl ester
N.M.R. (CDCl$_3$) δppm: 2.49 (s, 3H); 3.85 (s, 3H); 5.30 (s, 2H); 7.26~7.36 (m, 2H).
I.R. νNaCl (cm$^{-1}$): 2950, 1760, 1580, 1500, 1440, 1270, 1220, 1000, 800.
Mass: m/z 317 [M+]

(1-14) methyl [5-(5-phenyl-2-thienyl)tetrazol-1-yl] acetate (yield 47.1%)

Starting material: N-(5-phenyl-2-thenoyl)glycine methyl ester
M.P.=133-134° C.
N.M.R. (CDCl$_3$) δppm 3.85 (s, 3H); 5.38 (s, 2H); 7.39 (d, 1H, J=3.80 Hz); 7.40~7.48 (m, 3H); 7.55 (d, 1H, J=3.80 Hz); 7.63~7.66 (m, 2H).
I.R. νKBr (cm$^{-1}$); 3440, 1760, 1580, 1480, 1420, 1220, 750.
Mass: m/z 300 [M+]

(1-15) methyl [5-(3-methylcarbonylamino-2-thienyl)tetrazol-1-yl]-acetate; (yield 16.2%)

Starting material: N-(3-methylcarbonylamino-2-thenoyl)glycine methyl ester
M.P. 35-36° C.
N.M.R. (CDCl$_3$) δppm: 2.31 (s, 3H); 3.84 (s, 3H); 5.45 (s, 2H); 7.56 (d, 1H, J=5.20 Hz); 8.34 (d, 1H, J=5.20 Hz).
I.R. νKBr (cm$^{-1}$): 3240, 1750, 1580, 1490, 1440, 1220, 1180, 930, 750.
Mass: m/z 281 [M+]

(1-16) methyl [5-(3-propylcarbonylamino-2-thienyl)tetrazol-1-yl]-acetate; (yield 22.4%)

Starting material: N-(3-propylcarbonylamino-2-thenoyl)glycine methyl ester
M.P.=92-93° C.
N.M.R. (CDCl$_3$) δppm: 1.04 (t, 3H, J=7.3 Hz); 1.76~1.90 (m, 2H); 2.51 (t, 3H, J=7.30 Hz); 3.84 (s, 3H); 5.46 (s, 2H); 7.56 (d, 1H, J=5.50 Hz); 8.37 (d, 1H, J=5.50 Hz); 10.75 (bs, 1H).
I.R. νKBr (cm$^{-1}$): 3270, 2940, 1740, 1680, 1580, 1410, 1380, 1260, 1240, 1100, 760
Mass: m/z 309 [M+]

(1-17) methyl [5-(3-phenethylcarbonylamino-2-thienyl)tetrazol-1-yl] acetate; (yield 28.5%)

Starting material: N-(3-phenethylcarbonylamino-2-thenoyl)glycine methyl ester
M.P.=96-97° C.

N.M.R. (CDCl₃) δppm: 2.85 (t, 2H, J=7.70 Hz); 3.11 (t, 2H, J=7.70 Hz); 3.82 (s, 3H); 5.43 (s, 2H); 7.18~7.30 (m, 5H); 7.55 (d, 1H, J=5.50 Hz); 8.34 (d, 1H, J=5.50 Hz); 10.75 (bs, 1H).

I.R. νKBr (cm⁻¹): 3300, 1760, 1700, 1580, 1440, 1390, 1220, 1100.

Mass: m/z 371 . [M+]

(1-18) methyl [5-(5-methyl-2-furyl)tetrazol-1-yl] acetate; (yield 34.1%)

Starting material: N-(5-methyl-2-furoyl)glycine methyl ester

N.M.R. (CDCl₃) δppm: 2.39 (d, 3H, J=0.98 Hz); 3.80 (s, 3H); 5.45 (s, 2H); 6.25 (dq, 1H, J=3.66, 0.98 Hz); 7.23 (d, 1H, J=3.66 Hz).

I.R. νNaCl (cm⁻¹): 3120, 2950, 1740, 1620, 1570, 1440, 1220, 1020, 790.

Mass: m/z 222 [M+]

(1-19) methyl [5-(5-butyl-2-furyl)tetrazol-1-yl] acetate; (yield 27.2%)

Starting material: N-(5-5butyl-2-furoyl)glycine methyl ester

N.M.R. (CDCl₃) δppm: 0.95 (t, 3H, J=7.33 Hz); 1.31~1.45 (m, 2H); 1.57~1.70 (m, 2H); 2.70 (t, 2H, J=7.57 Hz); 3.79 (s, 3H); 5.45 (s, 2H); 6.24 (d, 1H, J=3.66 Hz); 7.24 (d, 1H, J=3.66 Hz).

I.R. νNaCl (cm⁻¹): 2950, 1760, 1620, 1560, 1440, 1220, 1020, 790.

Mass m/z 264 [M+]

(1-20) methyl [5-(5-bromo-2-furyl)tetrazol-1-yl] acetate; (yield 34%)

Starting material: N-(5-bromo-2-furoyl)glycine methyl ester

M.P.=106–107° C.

N.M.R. (CDCl₃) δppm: 3.84 (s, 3H); 5.45 (s, 2H); 6.58 (d, 1H, J=3.54 Hz); 7.31 (d, 1H, J=3.54 Hz).

I.R. νKBr (cm⁻¹): 3100, 3000, 1730, 1620, 1520, 1440, 1280, 1100, 1000, 780.

Mass: m/z 287 [M+]

1-21) methyl [5-(5-methylthio-2-furyl)tetrazol-1-yl] acetate; (yield 29%)

Starting material: N-(5-methylthio-2-furoyl)glycine methyl ester

N.M.R. (CDCl₃) δppm: 2.48 (s, 3H); 3.82 (s, 3H); 5.47 (s, 2H); 6.55 (d, 1H, J=3.66 Hz); 7.32 (d, 1H, J=3.66 Hz).

I.R. νNaCl (cm⁻¹): 3100, 2950, 1750, 1610, 1500, 1440, 1220, 1100, 1010, 780.

Mass: m/z 254 [M+]

(1-22) methyl [5-(2-bromo-3-furyl)tetrazol-1-yl] acetate; (yield 27.4%)

Starting material: N-(2-bromo-3-furoyl)glycine methyl ester

N.M.R. (CDCl₃) δppm: 3.81 (s, 3H); 5.23 (s, 2H); 6.70 (d, 1H, J=2.20 Hz); 7.52 (d, 1H, J=2.20 Hz).

I.R. νNaCl (cm⁻¹): 3150, 2950, 1750, 1620, 1530, 1440, 1220, 960.

Mass: m/z 287 . [M+]

(1-23) methyl [5-(2-(oct-4-yl)-3-furyl] tetrazol-1-yl] acetate; (yield 60.4%)

Starting material: N-[2(-oct-4-yl)-3-furoyl] glycine methyl ester

N.M.R. (CDCl₃) δppm: 0.82 (t, 6H, J=7.20 Hz); 1.10~1.27 (m, 6H); 1.52~1.70 (m, 4H); 3.25~3.31 (m, 1H); 3.81 (s, 3H); 5.16 (s, 2H); 6.40 (d, 1H, J=2.20 Hz); 7.48 (d, 1H, J=2.20 Hz).

I.R. νNaCl (cm⁻¹): 2950, 2850, 1750, 1620, 1530, 1440, 1220, 1000, 960.

Mass: m/z 320 [M+]

(1-24) methyl [5-(2-methylthio-3-furyl)tetrazol-1-yl] acetate; (yield 57.1%)

Starting material: N-[2-methylthio-3-furoyl)glycine methyl ester

M.P.=71–72° C.

N.M.R. (CDCl₃) δppm: 2.51 (s, 3H); 3.78 (s, 3H); 5.25 (s, 2H); 6.65 (d, 1H, J=2.20 Hz); 7.63 (d, 1H, J=2.20 Hz).

I.R. νNaCl (cm⁻¹): 3150, 2950, 1750, 1600, 1530, 1430, 1220, 960. 740.

Mass: m/z 254 [M+]

(1-25) methyl [5-(3-methylsulfonylamino-2-thienyl)tetrazol-1-yl] acetate: (yield 36.8%)

Starting material: N-(3-methylsulfonylamino-2-thenoyl)glycine methyl ester

M.P.=154–155° C.

N.M.R. (CDCl₃) δppm: 3.01 (s, 3H); 3.78 (s, 3H); 5.38 (s, 2H); 7.52 (d, 1H, J=5.61 Hz); 7.55 (d, 1H, J=5.61 Hz); 9.92 (bs, 1H).

I.R. νKBr (cm⁻¹): 3150, 3100, 1740, 1560, 1370, 1220, 1150, 760.

Mass: m/z 317 [M+]

(1-26) methyl [5-(3-butylsulfonylamino-2-thienyl)tetrazol-1-yl] acetate: (yield 74.4%)

Starting material: N-(3-butylsulfonylamino-2-thenoyl)glycine methyl ester

N.M.R. (CDCl₃) δppm: 0.87 (t, 3H, J=7.32 Hz); 1.35~1.44(m, 2H); 1.57~1.75 (m, 2H); 3.14 (t, 2H, J=7.94 Hz); 3.84 (s, 3H); 5.45 (s, 2H); 7.54 (d, 1H, J=5.49 Hz); 7.62 (d, 1H, J=5.49 Hz); 9.98 (bs, 1H).

I.R. νNaCl (cm⁻¹): 3100, 1750, 1560, 1370, 1220, 1150.

Mass: m/z 359 [M+]

(1-27) methyl [5-(3-phenylsulfonylamino-2-thienyl)tetrazol-1-yl] acetate: (yield 82.4%)

Starting material: N-(3-phenylsulfonylamino-2-thenoyl)glycine methyl ester

M.P.=124–125° C.

N.M.R. (CDCl₃) δppm: 3.72 (s, 3H); 5.23 (s, 2H); 7.31~7.47 (m, 5H); 7.53 (d, 1H, J=5.62 Hz); 7.58~7.91 (m, 2H); 10.16 (bs, 1H).

I.R. νKBr (cm⁻¹): 3120, 2950, 1750, 1560, 1520, 1430, 1380, 1240, 1160, 760, 580.

Mass: m/z 379 [M+]

(1-28) methyl [5-(2-methyl-3-furyl)tetrazol-1-yl] acetate: (yield 40.0%)

Starting material: N-(2-methyl-3-furoyl)glycine methyl ester

M.P.=54.5–56° C.

N.M.R. (CDCl₃) δppm: 2.58 (s, 3H); 3.82 (s, 3H); 5.19 (s, 2H); 6.44 (d, 1H, J=2.00 Hz); 7.45 (d, 1H, J=2.00 Hz).

I.R. νKBr (cm⁻¹): 3410, 3150, 1760, 1620, 1540, 1460, 1370, 1230.
Mass: m/z 222 [M⁺]

(1-29) methyl [5- [5-(N-methyl-N-[2-(methoxymethoxy)ethyl)-aminosulfonyl]-2-thienyl] tetrazol-1-yl] acetate: (yield 82.4%)

Starting material: N-[5- [N'-methyl-N'- [2-(methoxymethoxy)ethyl]-aminosulfonyl]-2-thenoyl)] glycine methyl ester N.M.R. (CDCl₃) δppm: 2.77 (s, 3H); 3.14 (t, 2H, J=5.37 Hz); 3.32 (s, 3H); 3.59 (t, 2H, J=5.37 Hz); 3.72 (s, 3H); 4.56 (s, 2H); 5.21 (s, 2H); 7.25 (d, 1H, J=5.13 Hz); 7.71 (d, 1H, J=5.13 Hz).

I.R. νKBr (cm⁻¹): 2950, 1750, 1440, 1350, 1220, 1150, 1040, 750, 710.
Mass: m/z 405 [M⁺]

EXAMPLE 2

(2-1) [5-(2-thienyl)tetrazol-1-yl] acetic acid 0.5 g (2.2 mM) of methyl [5-(2-thienyl)tetrazol-1-yl] acetate obtained in Example (1-1) was dissolved in 3 ml of methanol, 1 ml of a 4 N aqueous sodium hydroxide solution was added to the resulting solution at room temperature and the mixture was refluxed with heating for one hour. After cooling the mixture to room temperature, it was diluted with water, then impurities were removed with ethyl acetate and the aqueous phase was separated. The aqueous phase was acidified with hydrochloric acid, crystals precipitated out were filtered off, washed with water and recrystallized from a 50% ethanol-water mixture to give 0.39 g (yield 84.4%) of [5-(2-thienyl)tetrazol-1-yl] acetic acid.

M.P.=129-130° C. (decomposition)
N.M.R. (DMSO-d₆) δppm: 4.9~6.2 (br, 1H); 5.30 (s, 3H); 7.27~7.33 (m, 1H); 7.61 (dd, 1H, J=3.60, 1.20 Hz): 7.68 (dd, 1H, J=3.60, 1.20 Hz).
I.R νKBr (cm⁻¹): 3380, 1730, 1580, 1350, 1250.
Mass: m/z 210 [M⁺]

The following compounds were prepared in the same manner used in Example (2-1)

(2-2) [5-(3-methyl-2-thienyl)tetrazol-1-yl] acetic acid (yield=78%)

Starting Material: methyl [5-(3-methyl-2-thienyl)tetrazol-1-yl] acetate
M.P.=165-166° C. (decomposition)
N.M.R. (DMSO-d₆) δppm: 2.42 (s, 3H); 3.70 (bs, 1H); 5.20 (s, 2H); 7.06 (d, 1H, J=5.2 Hz); 7.53 (d, 1H, J=5.2 Hz).
I.R. νKBr (cm⁻¹): 3100, 2500, 1720, 1570, 1510, 1420, 1220.
Mass: m/z 224 [M⁺]

(2-3) [5-(4-methyl-2-thienyl)tetrazol-1-yl] acetic acid (yield=76%)

Starting Material: methyl [5-(4-methyl-2-thienyl)tetrazol-1-yl] acetate
M.P.=154-155° C. (decomposition)
N.M.R. (DMSO-d₆) δppm: 2.34 (s, 3H); 5.29 (bs, 3H); 7.22 (d, 1H, J=1.2 Hz); 7.41 (d, 1H, J=1.2 Hz).
I.R. νKBr (cm⁻¹): 3500, 2550, 1730, 1520, 1450, 1270, 1240, 1120.
Mass: m/z 224 [M⁺]

(2-4) [5-(5-methyl-2-thienyl)tetrazol-1-yl] acetic acid (yield=82%)

Starting Material: methyl. [5-(5-methyl-2-thienyl)tetrazol-1-yl] acetate
M.P.=150-151° C. (decomposition)
N.M.R. (DMSO-d₆) δppm: 2.58 (s, 3H); 5.28 (s, 2H); 5.90 (bs, 1H); 6.88~6.92 (m, 1H); 7.39~7.42 (m, 1H).
I.R. νKBr (cm⁻¹): 3400, 2990, 1730, 1580, 1520, 1440, 1260, 1240, 1000.
Mass: m/z 224 [M⁺]

(2-5) [5-(3-thienyl)tetrazol-1-yl] acetic acid (yield=71%)

Starting Material: methyl [5-(3-thienyl)tetrazol-1-yl] acetate
M.P.=172-173° C. (decomposition)
N.M.R. (DMSO-d₆) δppm: 3.33 (bs, 1H); 5.58 (s, 2H); 7.57-(dd, 1H, J=5.20, 1.20 Hz); 7.85 (dd, 1H, J=5.20, 2.80 Hz); 8.25 (dd, 1H, J=2.80, 1.20 Hz).
I.R. νKBr (cm⁻¹): 3380, 3120, 1730, 1580, 1280.
Mass: m/z 210 [M⁺]

(2-6) [5-(2-furyl)tetrazol-1-yl] acetic acid (yield=21%)

Starting Material: methyl [5-(2-furyl)tetrazol-1-yl] acetate
M.P.=157-158° C. (decomposition)
N.M.R. (CDCl₃-DMSO-d₆) δppm: 4.79 (bs, 1H); 5.45 (s, 2H); 6.81 (dd, 1H, J=3.60, 1.60 Hz); 7.37 (d, 1H, J=3.6 Hz); 8.08 (d, 1H, J=1.70 Hz).
I.R. νKBr (cm⁻¹): 3010, 2970, 2520, 1730, 1620, 1520, 1220, 1020.
Mass: m/z 194 [M⁺]

(2-7) [5-(3-furyl)tetrazol-1-yl] acetic acid (yield=30%)

Starting Material: methyl [5-(3-furyl)tetrazol-1-yl] acetate
M.P.=150-151° C. (decomposition)
N.M.R. (DMSO-d₆) δppm: 3.33 (bs, 1H); 5.56 (s, 2H); 7.00 (bs, 1H); 7.97 (bs, 1H); 8.46 (bs, 1H).
I.R. νKBr (cm⁻¹): 3370, 2430, 1720, 1620, 1350, 1240.
Mass: m/z 194 [M⁺]

(2-8) [5-(5-ethyl-2-thienyl)tetrazol-1-yl] acetic acid (yield=82%)

Starting Material: methyl [5-(5-ethyl 2-thienyl)tetrazol-1-yl] acetate
M.P.=131-138° C.
N.M.R. (DMSO-d₆) δppm: 1.36 (dt, 3H, J=7.70, 1.20 Hz); 2.93 (q, 2H, J=7.70 Hz); 3.28 (bs, 1H); 5.28 (s, 2H); 6.92 (dd, 1H, J=3.60, 1.20 Hz); 7.41 (dd, 1H, J=3.60, 1.20 Hz).
I.R. νKBr (cm⁻¹): 3490, 2950, 1740, 1580, 1500, 1410, 1220, 1110, 800.
Mass m/z 238 . [M⁺]

(2-9) [5-(5-benzyl-2-thienyl)tetrazol-1-yl] acetic acid (yield=77%)

Starting Material: methyl [5-(5-benzyl-2-thienyl)tetrazol-1-yl] acetate
M.P.=148-149° C.
N.M.R. (DMSO-d₆) δppm: 4.02 (s, 2H); 4.70 (bs, 1H); 5.25 (s, 2H); 6.92 (dd, 1H, J=3.60, 0.80 Hz); 7.23~7.38 (m, 5H); 7.41 (d, 1H, J=3.60).
I.R. (cm⁻¹): 2950, 1750, 1580, 1510, 1430, 1230.
Mass: m/z 300 [M⁺]

(2-10) [5-(5-methylthio-2-thienyl)tetrazol-1-yl] acetic acid (yield=67%)

Starting Material: methyl [5-(5-methylthio-2-thienyl)-tetrazol-1-yl] acetate
M.P.=179° C. (decomposition)
N.M.R. (DMSO-d$_6$) δppm: 2.61 (s, 3H); 5.34 (s, 2H); 7.10 (d, 1H, J=4.01 Hz); 7.49 (d, 1H, J=4.01 Hz).
I.R. νKBr (cm$^{-1}$): 3400, 1730, 1570, 1480, 1410, 1210.
Mass: m/z 256 [M$^+$]

(2-11) [5-(5-bromo-2-thienyl)tetrazol-1-yl] acetic acid (yield=67%)

Starting Material: methyl. [5-(5-bromo-2-thienyl)tetrazol-1-yl] acetate
M.P.=200° C. (decomposition)
N.M.R. (DMSO-d$_6$) δppm: 5.30 (s, 2H); 6.63 (bs, 1H); 7.19 (d, 1H, J=4.01 Hz); 7.34 (d, 1H, J=4.01 Hz).
I.R. νKBr (cm$^{-1}$): 3100, 2900, 1730, 1580, 1490, 1440, 1400, 1280, 1260, 1100, 980, 880. 800.
Mass: m/z 289 [M$^+$]

(2-12) [5-(2-methyl-3-thienyl)tetrazol-1-yl] acetic acid (yield=62%)

Starting Material: methyl [5-(2-methyl-3-thienyl)tetrazol-1-yl] acetate
M.P.=144° C. (decomposition)
N.M.R. (DMSO-d$_6$) δppm: 2.57 (s, 3H); 5.08 (s, 2H); 7.06 (d, 1H, J=5.20 Hz); 7.27 (d, 1H, J=5.20 Hz).
I.R. νKBr (cm$^{-1}$): 2900, 1740, 1570, 1440, 1400, 1340, 1260, 1220.
Mass: m/z 224 [M$^+$]

(2-13) [5-(5-bromomethyl-2-thienyl)tetrazol-1-yl] acetic acid (yield=66%)

Starting Material: methyl [5-(5-bromomethyl-2-thienyl)tetrazol-1-yl] acetate
M.P.=192° C. (decomposition)
N.M.R. (DMSO-d$_6$) δppm: 2.49 (s, 3H); 4.62 (bs, 1H); 5.28 (s, 2H); 7.39~7.41 (m, 2H).
I.R. νKBr (cm$^{-1}$): 3000, 1740, 1500, 1240, 1140.
Mass: m/z 303 [M$^+$]

(2-14) [5-(5-phenyl-2-thienyl)tetrazol-1-yl] acetic acid (yield=66%)

Starting Material: methyl [5-(5-phenyl-2-thienyl)tetrazol-1-yl] acetate
M.P.: 210° C. (decomposition)
N.M.R. (DMSO-d$_6$) δppm: 4.03 (bs, 1H); 5.36 (s, 2H) 7.36~7.48 (m, 3H); 7.42 (d, 1H, J=4.01 Hz); 7.58 (d, 1H, J=4.01 Hz); 7.64~7.67 (m, 2H).
I.R. νKBr (cm$^{-1}$): 3000, 1730, 1580, 1480, 1430, 1240, 1110, 760.
Mass: m/z 286 [M$^+$]

(2-15) [5-(3-methoxy-2-thienyl)tetrazol-1-yl] acetic acid (yield=72.1%)

Starting Material: methyl [5-(3-methoxy-2-thienyl)-tetrazol-1-yl] acetate
M.P.: 234° C. (decomposition)
N.M.R. (DMSO-d$_6$) δppm: 3.94 (s, 3H); 5.36 (s, 2H); 6.95 (d, 1H, J=5.50 Hz); 7.55 (d, 1H, J=5.50 Hz).
I.R. νKBr (cm$^{-1}$): 3110, 2950, 1740, 1580, 1520, 1440, 1250, 1200, 1070, 800, 750.
Mass: m/z 240 [M$^+$]

(2-16) [5-(3-butoxy-2-thienyl)tetrazol-1-yl] acetic acid (yield=65.6%)

Starting Material: methyl [5-(3-butoxy-2-thienyl)tetrazol-1-yl] acetate
M.P.: 197-198° C. (decomposition)
N.M.R. (DMSO-d$_6$) δppm: 0.95 (t, 3H, J=7.30 Hz); 1.34~1.41 (m, 2H); 1.70~1.81 (m, 2H); 4.13 (t, 2H, J=6.60 Hz); 4.80 (bs, 1H); 5.35 (s, 2H); 6.94 (d, 1H, J=5.50 Hz); 7.54 (d, 1H, J=5.50 Hz).
I.R. νKBr (cm$^{-1}$): 3500, 2950, 1730, 1570, 1510, 1400, 1250, 1200, 1070, 800, 750.
Mass: m/z 282 [M$^+$]

(2-17)
[5-(3-methylcarbonylamino-2-thienyl)tetrazol-1-yl] acetic acid; (yield=55.1%)

Starting Material: methyl [5-(3-methylcarbonylamino-2-thienyl)-tetrazol-1-yl] acetate
M.P.: 221° C. (decomposition)
N.M.R. (DMSO-d$_6$) δppm: 2.92 (s, 3H); 3.80~4.80 (br, 1H); 5.42 (s, 2H); 7.59 (d, 1H, J=5.40 Hz); 8.28 (d, 1H, J=5.40 Hz).
I.R. νKBr (cm$^{-1}$): 3250, 2920, 1740, 1650, 1580, 1440, 1390, 1240, 1220, 1110, 760.
Mass: m/z 267 [M$^+$]

(2-18)
[5-(3-propylcarbonylamino-2-thienyl)tetrazol-1-yl] acetic acid; (yield=69.6%)

Starting Material: methyl [5-(3-propylcarbonylamino 2-thienyl)-tetrazol-1-yl] acetate
M.P.: 192° C. (decomposition)
N.M.R. (DMSO-d$_6$) δppm: 1.03 (t, 3H, J=7.30 Hz); 1.74~1.88 (m, 2H); 2.19 (t, 2H, J=7.30 Hz); 4.40~5.60 (br, 1H); 5.41 (s, 2H); 7.59 (d, 1H, J=5.50 Hz); 8.30 (d, 1H, J=5.50 Hz); 10.74 (bs, 1H).
I.R. νKBr(cm$^{-1}$): 3310, 2960, 1720, 1590, 1530, 1440, 1180, 760.
Mass: m/z 295 [M$^+$]

(2-19)
[5-(3-phenethylcarbonylamino-2-thienyl)tetrazol-1-yl] acetic acid; (yield=59.7%)

Starting Material: methyl [5-(3-phenethylcarbonylamino-2-thienyl) tetrazol-1-yl] acetate
M.P.: 178° C. (decomposition)
N.M.R. (DMSO-d$_6$) δppm: 2.83 (t, 2H, J=7.70 Hz); 3.09 (t, 2H, J=7.70 Hz); 4.22 (bs, 1H); 5.39 (s, 2H); 7.18~7.30 (m, 5H); 7.60 (d, 1H, J=5.50 Hz); 8.27 (d, 1H, J=5.50 Hz); 10.72 (bs, 1H).
I.R. νKBr (cm$^{-1}$): 3450, 2920, 1740, 1640, 1580, 1440, 1400, 1220, 1110.
Mass: m/z 357 [M$^+$]

(2-20) [5-(5-butyl-2-thienyl)tetrazol-1-yl] acetic acid (yield=89%)

Starting Material: methyl [5-(5-butyl-2-thienyl)tetrazol-1-yl] acetate
M.P.: 103-104° C.
N.M.R. (CDCl$_3$+DMSO-d$_6$) δppm: 0.95 (t, 3H, J=7.33 Hz); 1.35~1.49 (m, 2H); 1.65~1.76 (m, 2H); 2.89 (t, 2H, J=7.33 Hz); 5.27 (s. 2H); 6.89 (d, 1H, J=3.66 Hz); 7.41 (d, 1H, J=3.66 Hz).
I.R. νKBr (cm$^{-1}$): 2920, 1730, 1580, 1520, 1420, 1220, 800.
Mass: m/z 266 [M$^+$]

(2-21) [5-(5-phenylpropyl-2-thienyl)tetrazol-1-yl] acetic acid (yield=89.8%)

Starting Material: methyl [5-(5-phenylpropyl 2-thienyl)-tetrazol-1-yl] acetate
M.P.: 85–86° C.
N.M.R. (CDCl$_3$+DMSO-d$_6$) δppm: 2.06 (quint., 2H, J=7.57 Hz); 2.71 (t, 2H, J=7.57 Hz); 2.91 (t, 2H, J=7.57 Hz); 4.98 (bs, 1H); 5.28 (s, 2H); 6.91 (d, 1H, J=3.80 Hz); 7.18~7.33 m, 5H); 7.42 (d, 1H, J=3.80 Hz).
I.R. νKBr (cm$^{-1}$): 2920, 1720, 1580, 1510, 1420, 1220, 1130, 800.
Mass: m/z 328 [M+]

(2-22) [5-(5-methoxymethyl-2-thienyl)tetrazol-1-yl] acetic acid (yield=48.9%)

Starting Material: methyl [5-(5-methoxymethyl-2-thienyl)-tetrazol-1-yl] acetate
M.P.: 124–125° C.
N.M.R. (CDCl$_3$+DMSO-d$_6$) δppm: 3.43 (s, 3H); 4.67 (d, 2H, J=0.73 Hz); 5.29 (s, 2H); 7.10 (dt, 1H, J=3.66, 0.73 Hz); 7.49 (d, 1H, J=3.66 Hz).
I.R. νKBr (cm$^{-1}$): 2900, 1740, 1580, 1420, 1220, 1020, 800.
Mass: m/z 254 [M+]

(2-23) [5-(5-butoxymethyl-2-thienyl)tetrazol-1-yl] acetic acid (yield=82.3%)

Starting Material: methyl [5-(5-butoxymethyl-2-thienyl)-tetrazol-1-yl] acetate
M.P.: 67–68° C.
N.M.R. (CDCl$_3$+DMSO-d$_6$) δppm: 0.93 (t, 3H, J=7.20 Hz); 1.38~1.47 (m, 2H); 1.55~1.66 (m, 2H); 3.54 (t, 2H, J=6.47 Hz); 4.67 (d, 2H, J=0.73 Hz); 4.07 (s, 2H); 5.27 (s, 2H); 7.07 (d, 1H, J=3.79 Hz); 7.47 (d, 1H, J=3.79 Hz).
I.R. νKBr (cm$^{-1}$): 2950, 1730, 1580, 1420, 1230, 1090, 800.
Mass: m/z 296 [M+]

(2-24) [5-(2-bromo-3-thienyl)tetrazol-1-yl] acetic acid (yield=48.9%)

Starting Material: methyl [5-(2-bromo-3-thienyl)tetrazol-1-yl] acetate
M.P.: 145–146° C.
N.M.R. (CDCl$_3$+DMSO-d$_6$) δppm: 4.56 (bs, 1H); 5.10 (s, 2H); 7.12 (d, 1H, J=5.18 Hz); 7.47 (d, 1H, J=5.18 Hz).
I.R. νKBr (cm$^{-1}$): 2950, 1740, 1570, 1440, 1220, 1000, 800, 720.
Mass: m/z 289 [M+]

(2-25) [5- [2-(oct-4-yl)-3-thienyl] tetrazol-1-yl] acetic acid (yield=80.6%)

Starting Material: methyl [5-[2-(oct-4-yl)-3-thienyl] tetrazol-1-yl] acetate
M.P.: 79–80° C.
N.M.R. (CDCl$_3$+DMSO-d$_6$) δppm: 0.78~0.84 (m, 6H); 1.13~1.25 (m, 6H); 1.45~1.71 (m, 4H); 3.15~3.22 (m, 1H); 5.00 (s, 2H); 7.01 (d, 1H, J=5.37 Hz); 7.36 (dd, 1H, J=5.37, 0.73 Hz).
I.R. νKBr (cm$^{-1}$): 2900, 1740, 1570, 1110, 1220, 720.
Mass: m/z 322 . [M+]

(2-26) [5-(2-methylthio-3-thienyl)tetrazol-1-yl] acetic acid (yield=75.3%)

Starting Material: methyl [5-(2-methylthio-3-thienyl)-tetrazol-1-yl] acetate
M.P.: 134–135° C.
N.M.R. (CDCl$_3$+DMSO-d$_6$) δppm: 2.51 (s, 3H); 5.14 (s, 2H); 7.18 (d, 1H, J=5.50 Hz); 7.47 (d, 1H, J=5.50 Hz).
I.R. νKBr (cm$^{-1}$): 3100, 2900, 1730, 1550, 1440, 1220, 800,
Mass: m/z 256 [M+]

(2-27) [5-(5-methyl-2-furyl)tetrazol-1-yl] acetic acid (yield=42.7%)

Starting Material: methyl [5-(5-methyl-2-furyl)tetrazol-1-yl] acetate
M.P. 150–151° C. (decomposition)
N.M.R. (CDCl$_3$+DMSO-d$_6$) δppm: 2.41 (s, 3H); 5.40 (s, 2H); 6.23 (dd, 1H, J=3.42, 0.98 Hz); 7.20 (d, 1H, J=3.42 Hz).
I.R. νKBr (cm$^{-1}$): 3500, 3100, 1720, 1570, 1440, 1240, 800.
Mass: m/z 208 [M+]

(2-28) [5-(5-butyl-2-furyl)tetrazol1-yl-] acetic acid (yield=63.4%)

Starting Material: methyl. [5-(5-butyl-2-furyl)tetrazol-1-yl] acetate
M.P.: 109–110° C.
N.M.R. (CDCl$_3$+DMSO-d$_6$) δppm: 0.95 (t, 3H, J=7.20 Hz); 1.32~1.46 (m, 2H); 1.62~1.73 (m, 2H); 2.72 (t, 2H, J=7.56 Hz); 5.40 (s, 2H); 6.24 (d, 1H, J=3.42 Hz); 7.19 (d, 1H, J=3.42 Hz).
I.R. νKBr (cm$^{-1}$): 2900, 1740, 1560, 1450, 1200, 800.
Mass: m/z 250 [M+]

(2-29) [5-(5-bromo-2-furyl)tetrazol-1-yl] acetic acid (yield=73.6%)

Starting Material: methyl [5-(5-bromo-2-furyl)tetrazol-1-yl] acetate
M.P.: 159–160° C. (decomposition)
N.M.R. (CDCl$_3$+DMSO-d$_6$) δppm: 5.41 (s, 2H); 6.60 (d, 1H, J=3.66 Hz); 7.27 (d, 1H, J=3.66 Hz).
I.R. νKBr (cm$^{-1}$): 3150, 3000, 1730, 1600, 1420, 1200, 740.
Mass: m/z 273 [M+]

(2-30) [5-(5-methylthio-2-furyl)tetrazol-1-yl] acetic acid (yield=42.3%)

Starting Material: methyl [5-(5-methylthio-2-furyl)-tetrazol-1-yl] acetate
M.P.: 160.5–161.5° C. (decomposition)
N.M.R. (CDCl$_3$+DMSO-d$_6$) δppm: 2.51 (s, 3H); 5.43 (s, 2H); 6.55 (d, 1H, J=3.66 Hz); 7.28 (d, 1H, J=3.66 Hz).
I.R. νKBr (cm$^{-1}$): 3100, 3000, 1730, 1620, 1500, 1440, 1210, 1200, 800.
Mass: m/z 240 [M+]

(2-31) [5-(2-bromo-3-furyl)tetrazol-1-yl] acetic acid (yield=60.5%)

Starting Material: methyl [5-(2-bromo-3-furyl)tetrazol-1-yl] acetate
M.P.: 138–139° C. (decomposition)
I.R. (CDCl$_3$+DMSO-d$_6$) δppm: 5.17 (s, 2H); 4.33 (bs, 1H); 6.74 (d, 1H, J=2.20 Hz); 7.54 (d, 1H, J=2.20 Hz).

I.R. νKBr (cm⁻¹): 3100, 3000, 1720, 1620, 1520, 1440, 1260, 1100, 1010, 930
Mass m/z 273 [M+]

(2-32) [5-(2-methylthio-3-furyl)tetrazol-1-yl] acetic acid (yield=78%)

Starting Material: methyl [5-(2-methylthio-3-furyl)-tetrazol-1-yl] acetate
M.P.: 120–122° C.
N.M.R. (CDCl$_3$+DMSO-d$_6$) δppm: 2.53 (s, 3H); 4.09~4.65 (br, 1H); 5.43 (s, 2H); 6.71 (d, 1H, J=1.95 Hz); 7.67 (d, 1H, J=1.95 Hz).
I.R. νKBr (cm⁻¹): 3300, 3150, 2950, 1730, 1590, 1440, 1220, 960, 810, 740.
Mass: m/z 240 [M+]

(2-33) [5-(2-phenylthio-3-thienyl)tetrazol-1-yl] acetic acid (yield=67.6%)

Starting Material: methyl [5-(2-phenylthio-3-thienyl)-tetrazol-1-yl] acetate
M.P.: 133–134° C. (decomposition)
N.M.R. (CDCl$_3$+DMSO-d$_6$) δppm: 5.50 (s, 2H); 7.23~7.29 (m, 6H); 7.59 (d, 1H, J=5.30 Hz).
I.R. νKBr (cm⁻¹): 3100, 3000, 1720, 1570, 1480, 1430, 1390, 1260 870, 730.
Mass: m/z 318 [M+]

(2-34) [5-(5-phenylthio-2-thienyl)tetrazol-1-yl] acetic acid (yield=61.0%)

Starting Material: methyl [5-(5-phenylthio-2-thienyl)-tetrazol-1-yl] acetate
M.P.: 125–126° C. (decomposition)
N.M.R. (CDCl$_3$+DMSO-d$_6$) δppm: 3.37 (bs, 1H); 5.29 (s, 2H); 7.27~7.38 (m, 6H); 7.51 (d, 1H, J=3.90 Hz).
I.R. νKBr (cm⁻¹): 3000, 1730, 1580, 1480, 1430, 1410, 1220, 1130, 800, 730.
Mass m/z 318 [M+]

(2-35) [5- [5-(N,N-diethylaminosulfonyl)-2-thienyl] tetrazol-1-yl acetic acid (yield=80.0%)

Starting Material: methyl [5- [5-(N,N-diethylaminosulfonyl)-2-thienyl] tetrazol-1-yl] acetate
M.P.: 134–135° C.
N.M.R. (CDCl$_3$+DMSO-d$_6$) δppm: 1.01 (t, 6H, J=7.08 Hz); 3.10 (q, 4H, J=7.08 Hz); 3.32 (bs, 1H); 5.25 (s, 2H); 7.23 (d, 1H, J=5.13 Hz); 8.18 (d, 1H, J=5.13 Hz).
I.R. νKBr (cm⁻¹): 3100, 2970, 1740, 1410, 1360, 1220, 1150, 940, 700, 590.
Mass: m/z 333 [m+]

(2-36) [5- [5-(N,N-dibutylaminosulfonyl)-2-thienyl] tetrazol-1-yl acetic acid (yield=61.0%)

Starting Material: methyl [5-[5-(N,N-dibutylaminosulfonyl)-2-thienyl] tetrazol-1-yl] acetate
N.M.R. (CDCl$_3$) δppm: 0.79 (t, 6H, J=7.32 Hz); 1.09~1.23 (m, 4H); 1.30~1.41 (m, 4H); 2.87 (t, 4H, J=7.57 Hz); 5.14 (s, 2H); 7.11 (d, 1H, J=5.12 Hz); 7.61 (d, 1H, J=5.12 Hz).
I.R. νNaCl (cm⁻¹): 2950, 1740, 1340, 1220, 1150.
Mass: m/z 401 [M+]

(2-37) [5-(5-piperidinosulfonyl2-thienyl)tetrazol-1-yl] acetic acid; (yield=55.0%)

Starting Material: methyl [5-(5-piperidinosulfonyl-2-thienyl)-tetrazol-1-yl] acetate
M.P.: 143–146° C.

N.M.R. (CDCl$_3$) δppm: 1.38~1.39 (m, 2H); 1.48~1.58 (m, 4H); 2.86 (t, 4H, J=5.37 Hz); 5.15 (s, 2H); 7.16 (d, 1H, J=5.13 Hz); 7.66 (d, 1H, J=5.13 Hz).
I.R. νKBr (cm⁻¹): 3450, 2950, 1735, 1340, 1230, 1160.
Mass: m/z 357 [M+]

(2-38) [5-[2-(N,N-diethylaminosulfonyl)]-3-thienyl)tetrazol-1-yl] acetic acid; (yield=66.1%)

Starting Material: methyl [5- [2-(N,N-diethylaminosulfonyl)-5-trimethylsilyl-3-thienyl] tetrazol-1-yl] acetate
M.P.: 128.5–130° C.
N.M.R. (CDCl$_3$) δppm: 1.00 (t, 6H, J=7.08 Hz); 3.00 (q, 4H, J=7.08 Hz); 5.13 (s, 2H); 7.10 (d, 1H, J=4.88 Hz); 7.62 (d, 1H, J=4.88 Hz).
I.R. νKBr (cm⁻¹): 2950, 1740, 1340, 1220, 1140.
Mass: m/z 331 [M+]

(2-39) [5-(3-methylsulfonylamino-2-thienyl)tetrazol-1-yl] acetic acid; (yield=36.8%)

Starting Material: methyl [5-(3-methylsulfonylamino-2-thienyl) tetrazol-1-yl] acetate
M.P.: 154–155° C.
N.M.R. (CDCl$_3$) δppm: 3.01 (s, 3H); 3.78 (s, 3H); 5.38 (s, 2H); 7.53 (d, 1H, J=5.61 Hz); 7.62 (d, 1H, J=5.61 Hz); 9.92 (bs, 1H).
I.R. νKBr (cm⁻¹): 3150. 3100, 1740, 1560, 1370, 1330, 1220, 1150, 760.
Mass: m/z 303 [M+]

(2-40) [5-(3-butylsulfonylamino-2-thienyl)tetrazol-1-yl] acetic acid; (yield=74.4%)

Starting Material: methyl [5-(3-butylsulfonylamino-2-thienyl) tetrazol-1-yl] acetate
M.P.: 158–159° C. (decomposition)
N.M.R. (CDCl$_3$) δppm: 0.87 (t, 3H, J=7.32 Hz); 1.35~1.44 (m, 2H); 1.75~1.85 (m, 2H); 3.14 (t, 2H, J=7.95 Hz); 3.84 (s, 3H); 5.45 (s, 2H); 7.54 (d, 1H, J=5.49 Hz); 7.62 (d, 1H, J=5.49 Hz); 9.98 (bs, 1H).
I.R. νKBr (cm⁻¹): 3100, 2950, 1750, 1560, 1370, 1220, 1150.
Mass: m/z 345 [M+]

(2-41) [5-(3-phenylsulfonylamino-2-thienyl)tetrazol-1-yl] acetic acid; (yield=82.4%)

Starting Material: methyl [5-(3-phenylsulfonylamino)-2-thienyl) tetrazol-1-yl] acetate
M.P.: 124–125° C.
N.M.R. (CDCl$_3$) δppm: 3.72 (s, 3H); 5.23 (s, 2H); 7.31~7.17 (m. 5H); 7.53 (d. 1H, J=5.62 Hz); 7.58~7.91 (m, 2H): 10.16 (bs, 1H).
I.R. νKBr (cm⁻¹): 3120, 2950, 1750, 1560, 1520, 1430. 1380, 1240, 1160, 760, 580.
Mass: m/z 365 [M+]

(2-42) [5-(3-hydroxy-2-thienyl)tetrazol-1-yl] acetic acid (yield=73.6%)

Starting Material: methyl [5-(3-hydroxy-2-thienyl)-tetrazol-1-yl] acetate
M.P.: 199–200° C. (decomposition)
N.M.R. (CDCl$_3$) δppm: 4.36 (bs, 1H); 5.38 (s, 2H); 6.87 (d, 1H, J=5.37 Hz); 7.45 (d, 1H, J=5.37 Hz); 10.23 (bs, 1H).
I.R. νKBr (cm⁻¹): 3450, 2850, 1720, 1440, 1230, 1120, 1010, 750.

Mass: m/z 226 [M+]

(2-43) [5-(2-methylsulfinyl-3-thienyl)tetrazol-1-yl ] acetic acid; (yield = 20.4%)

Starting Material: methyl [5-(2-methylsulfinyl-3-thienyl)-tetrazol-1-yl] acetate
M.P.: 144-145° C.
N.M.R. (CDCl$_3$+DMSO-d$_6$) δppm: 3.08 (s, 3H); 5.15 (d, 1H, J=17.82 Hz); 5.30 (d, 1H, J=17.82 Hz); 7.34 (d, 1H, J=5.12 Hz); 7.81 (d, 1H, J=5.12 Hz).
I.R. νKBr (cm$^{-1}$): 3100, 2900, 1700, 1570, 1420, 1300, 1260, 1220, 1000, 760.
Mass: m/z 272 [M+]

(2-44) [5-(2-methylsulfonyl-3-thienyl)tetrazol-1-yl] acetic acid; (yield = 76.1%)

Starting Material: methyl [5-(2-methylsulfonyl-3-thienyl)-tetrazol-1-yl ] acetate
M.P.: 135-136° C.
N.M.R. (CDCl$_3$+DMSO-d$_6$) δppm: 3.32 (bs, 1H); 3.48 (s, 3H); 5.37 (s, 2H); 7.40 (d, 1H, J=5.13 Hz); 8.32 (d, 1H, J=5.13 Hz).
I.R. νKBr (cm$^{-1}$): 3500 3100, 3000, 1720, 1310, 1140, 950, 760.
Mass: m/z 288 [M+]

(2-45) [5-(3-amino-2-thienyl)-tetrazol-1-yl] acetic acid hydrochloride; (yield = 76.1%)

Starting Material: methyl [5-(3-methylcarbonylamino 2-thienyl)-tetrazol-1-yl] acetate
M.P.: 258° C. (decomposition)
N.M.R. (DMSO-d$_6$) δppm: 2.34 (bs, 1H); 5.17 (s, 2H); 7.02 (d, 1H, J=5.50 Hz); 7.59 (d, 1H, J=5.50 Hz); 11.01 (bs, 1H).
I.R. νKBr (cm$^{-1}$): 3240, 3160, 1700, 1590, 1530, 1380, 1040, 770.

(2-46) [5-[5-[N-methyl-N-(2-hydroxyethyl)aminosulfonyl]-2-thienyl] tetrazol-1-yl ] acetic acid; (yield = 76.1%)

Starting Material: methyl [5- [5- [N-methyl-N- [2-(methoxyethoxy)-ethyl] aminosulfonyl]-2-thienyl] -tetrazol-1-yl] acetate
N.M.R. (CD$_3$OD) δppm: 2.77 (s, 3H); 3.07 (t, 2H, J=5.61 Hz); 3.60 (t, 2H, J=5.61 Hz); 5.24 (s, 2H); 7.26 (d, 1H, J=5.13 Hz); 8.02 (d, 1H, J=5.13 Hz).
I.R. νNaCl (cm$^{-1}$): 3450, 2950, 1740, 1440, 1350, 1150, 1040, 590.
Mass: m/z 347 [M+]

EXAMPLE 3

(3-1) methyl [5-(2-thienyl)tetrazol-1-yl] acetate

To a solution of 500 mg (2.51 mM) of N-(2-thenoyl)glycine methyl ester in 5 ml of anhydrous methylene chloride, there were added, at room temperature, 185 mg (2.53 mM) of anhydrous N,N-dimethylformamide and 418 mg (3.51 mM) of thionyl chloride and then the mixture was refluxed for one hour. The reaction solution was concentrated at 40° C. under reduced pressure and the resulting residue was dissolved in 5 m l of anhydrous N,N-dimethylformamide.

The resulting solution was dropwise added to a suspension of 410 mg (6.3 mM) of sodium azide in 3 ml of anhydrous N,N dimethylformide at a temperature of the suspension ranging from 5° to 10° C. over 30 minutes with stirring. After the dropwise addition, the reaction mixture was stirred for additional 30 minutes at room temperature, poured into ice-water and extracted with ethyl acetate. The organic phase obtained was washed with water, dried over anhydrous sodium sulfate and then concentrated under reduced pressure. The resultant residue was recrystallized from ethyl acetate/n hexane to give 395 mg (yield 70.2%) of methyl [5-(2-thienyl)tetrazol-1-yl] acetate.

The results of the instrumental analysis of this product are consistent with those for the product obtained in Example (1-1).

(3-2) ethyl [5-(3-thienyl)tetrazol-1-yl] acetate

To a solution of 1 g (4.69 mM) of N-(3-thenoyl)glycine methyl ester in 10 ml of anhydrous methylene chloride, there were added, at room temperature, 350 mg (4.79 mM) of anhydrous N,N-dimethylformamide and 800 mg (6.72 mM) of thionyl chloride and then the mixture was refluxed for one hour. The reaction solution was concentrated at 40° C. under reduced pressure and the resulting residue was dissolved in 10 ml of anhydrous N,N-dimethylformamide.

The resulting solution was dropwise added to a suspension of 800 mg (12.3 mM) of sodium azide in 5 ml of anhydrous N,N-dimethylformamide at a temperature of the suspension ranging from 5° to 10° C. over 30 minutes with stirring. After the dropwise addition, the reaction mixture was stirred for additional 30 minutes at room temperature, poured into ice-water and extracted with ethyl acetate. The organic phase obtained was washed with water, dried over anhydrous sodium sulfate and then concentrated under reduced pressure. The resultant residue was recrystallized from ethyl acetate/n hexane to give 730 mg (yield 65.3%) of ethyl [5-(3-thienyl)tetrazol-1-yl] acetate.
M.P.: 69.5-70.5° C.
N.M.R. (CDCl$_3$) δppm: 1.27 (t, 3H, J=7.25 Hz); 4.26 (g, 2H, J=7.25 Hz); 5.25 (s, 2H); 7.48 (dd, 1H, J=5.20, 1.21 Hz); 7.55 (dd, 1H, J=5.20, 2.82 Hz); 7.84 (dd, 1H, J=2.82, 1.21 Hz).
I.R. νKbr (cm$^{-1}$): 3100, 2970, 2950, 1740, 1570, 1440, 1370, 1210, 880.
Mass: m/z 238 [M+]

The following compounds were prepared in the same manner as described above.

(3-3) methyl [5-(3-methoxy-2-thienyl)tetrazol-1-yl] acetate (yield = 12%)

Starting Material: N-(3-methoxy-2-thenoyl)glycine methyl ester
M.P.: 121-122° C.
N.M.R. (CDCl$_3$) δppm: 3.76 (s, 3H); 3.90 (s, 3H); 5.34 (s, 2H); 6.97 (d, 1H, J=5.64 Hz); 7.54 (d, 1H, J=5.64 Hz).
I.R. νKBr (cm$^{-1}$):3100, 2950, 1760, 1580, 1520, 1400, 1240, 1220, 1070, 760.
Mass: m/z 254 [M+]

(3-4) methyl [5-(3-butoxy-2-thienyl)tetrazol-1-yl] acetate (yield = 13%)

Starting Material: N-(3-butoxy-2-thenoyl)glycine methyl ester
M.P.: 62-62.5° C.
N.M.R. (CDCl$_3$) δppm: 0.88 (t, 3H, J=7.26 Hz); 1.28~1.39 (m, 2H); 1.59~1.70 (m, 2H); 3.66 (s, 3H); 4.04 (t, 2H, J=6.85 Hz); 5.34 (s, 2H); 6.84 (d, 1H, J=5.64 Hz); 7.45 (d, 1H, J=5.64 Hz).
I.R. νKBr (cm$^{-1}$); 3100, 2950, 1760, 1580, 1510, 1400, 1240, 1220, 1050, 750.

Mass: m/z 296 [M+]

(3-5) methyl [5-(5-butyl-2-thienyl)tetrazol-1-yl] acetate (yield=63.8%)

Starting Material: N-(5-butyl-2-thenoyl)glycine methyl ester
M.P.: 58-59° C.
N.M.R. (CDCl$_3$) δppm: 0.95 (t, 3H, J=7.32 Hz); 1.37~1.46 (m, 2H); 1.65~1.76 (m, 2H); 2.88 (t, 2H, J=7.32 Hz); 3.83 (s, 3H); 5.32 (s, 2H); 6.89 (d, 1H, J=3.66 Hz); 7.38 (d, 1H, J=3.66 Hz).
I.R. νKBr (cm$^{-1}$): 2950, 1740, 1580, 1520, 1440, 1380, 1220, 1100, 1000, 800.
Mass m/z 280 [M+]

(3-6) methyl [5-(5-phenylpropyl-2-thienyl)tetrazol-1-yl] acetate (yield - 74.1%)

Starting Material: N-(5-phenylpropyl-2-thenoyl)glycine methyl ester
N.M.R. (CDCl$_3$) δppm: 2.06 (quint., 2H, J=7.57 Hz); 2.71 (t, 2H, J=7.57 Hz); 2.91 (t, 2H, J=7.57 Hz); 3.83 (s, 3H); 5.31 (s, 2H); 6.90 (dt, 1H, J=3.72 0.73 Hz); 7.18~7.34 (m, 5H); 7.40 (d, 1H, J=3.72 Hz).
I.R. νNaCl (cm$^{-1}$): 2920, 1750, 1580. 1500, 1440, 1220, 1100, 700.
Mass: m/z 342 [M+]

(3-7) methyl [5-(5-methoxymethyl-2-thienyl)tetrazol-1-yl] acetate (yield=72.5%)

Starting Material: N-(5-methoxymethyl-2-thenoyl)glycine methyl ester
N.M.R. (CDCl$_3$) δppm: 3.44 (s, 3H); 3.84 (s, 3H); 4.67 (d, 2H, J=0.73 Hz); 5.33 (s, 2H); 7.10 (dt, 1H, J=3.66, 0.73 Hz); 7.48 (d, 1H, J=3.66 Hz).
I.R. νNaCl (cm$^{-1}$): 2950, 1750, 1580, 1440, 1360, 1220, 1000, 800.
Mass: m/z 268 [M+]

(3-8) methyl [5-(5-butoxymethyl-2-thienyl)tetrazol-1-yl] acetate (yield=68.9%)

Starting Material: N-(5-butoxymethyl-2-thenoyl)glycine methyl ester
M.P.: 48-49° C.
N.M.R. (CDCl$_3$) δppm: 0.93 (t, 3H, J=7.21 Hz); 1.33~1.45 (m, 2H); 1.56~1.66 (m, 2H); 3.54 (t, 2H, J=6.74 Hz); 3.83 (s, 3H); 4.70 (d, 2H, J=0.73 Hz); 5.33 (s, 2H); 7.07 (dt, 1H, J=3.72, 0.73 Hz); 7.46 (d, 1H, J=3.72 Hz).
I.R. νKBr (cm$^{-1}$): 2950, 2850, 1740, 1580, 1420, 1230, 1100, 800.
Mass: m/z 310 [M+]

(3-9) methyl [5-(2-bromo-3-thienyl)tetrazol-1-yl] acetate (yield=45.9%)

Starting Material: N-(2-bromo-3-thenoyl)glycine methyl ester
N.M.R. (CDCl$_3$) δppm: 3.76 (s, 3H); 5.17 (s, 2H); 7.10 (d, 1H, J=5.73 Hz); 7.48 (d, 1H, J=5.73 Hz).
I.R. νNaCl (cm$^{-1}$): 3100, 2950, 1750, 1580, 1430, 1220, 1000
Mass: m/z 303 [M+]

(3-10) methyl [5- 2-(oct-4-yl)-3-thienyl] tetrazol-1-yl] acetate (yield=35.5%)

Starting Material: N- [2 (oct-4-yl)-3-thenoyl] glycine methyl ester
N.M.R. (CDCl$_3$) δppm: 0.78~0.85 (m, 6H); 1.11~1.26 (m, 6H); 1.50~1.67 (m, 4H); 3.12~3.18 (m, 1H); 3.81 (s, 3H); 5.05 (s, 2H); 6.93 (d, 1H, J=5.37 Hz); 7.36 (d, 1H, J=5.37 Hz).
I.R. νNaCl (cm$^{-1}$): 2950, 2850, 1760, 1440, 1220.
Mass: m/z 336 [M+]

(3-11) methyl [5-(2-methylthio-3-thienyl)tetrazol-1-yl] acetate (yield=70.8%)

Starting Material: N-(2-methylthio-3-thenoyl)glycine methyl ester
M.P.: 90-91° C.
N.M.R. (CDCl$_3$) δppm: 2.47 (s, 3H); 3.75 (s, 3H); 5.20 (s, 2H); 7.15 (d, 1H, J=5.37 Hz); 7.46 (d, 1H, J=5.37 Hz).
I.R. νKBr (cm$^{-1}$): 3110, 2920, 1750, 1550, 1420, 1220, 1100.
Mass: m/z 270 [M+]

(3-12) methyl [5-(2-phenylthio-3-thienyl)tetrazol-1-yl] acetate (yield=78.6%)

Starting Material: N-(2-phenylthio-3-thenoyl)glycine methyl ester
N.M.R. (CDCl$_3$) δppm: 3.73 (s, 3H); 5.10 (s, 2H); 7.21~7.27 (m, 6H); 7.55 (d, 1H, J=5.37 Hz).
I.R. νNaCl (cm$^{-1}$): 3100, 2950, 1750, 1570, 1480, 1440, 1360, 1220, 1000.
Mass: m/z 332 [M+]

(3-13) methyl [5-(5-phenylthio-2-thienyl)tetrazol-1-yl] acetate (yield=70.8%)

Starting Material: N-(5-phenylthio-2-thenoyl)glycine methyl ester
M.P.: 102-103° C.
N.M.R. (CDCl$_3$) δppm: 3.82 (s, 3H); 5.30 (s, 2H); 7.26~7.37 (m, 6H); 7.49 (d, 1H, J=3.91 Hz).
I.R. νKBr (cm$^{-1}$): 2900, 1750, 1570, 1480, 1430, 1410, 1360, 1220, 1100, 800.
Mass: m/z 332 [M+]

(3-14) methyl [5-[5-(N,N-diethylaminosulfonyl)-2-thienyl] tetrazol-1-yl] acetate; (yield=72.5%)

Starting Material: N-[5-(N',N'-diethylaminosulfonyl)-2-thenoyl)-glycine methyl ester
N.M.R. (CDCl$_3$) δppm: 1.08 (t, 6H, J=7.20 Hz); 3.07 (q, 4H, J=7.20 Hz); 3.72 (s, 3H); 5.23 (s, 2H); 7.22 (d, 1H, J=5.12 Hz); 7.67 (d, 1H, J=5.12 Hz).
I.R. νNaCl (cm$^{-1}$): 3100; 2950, 1750, 1610, 1440, 1350, 1220, 1150, 940, 700.
Mass: m/z 347 [M+]

(3-15) methyl [5-[5-(N,N-dibutylaminosulfonyl)-2-thienyl] tetrazol-1-yl] acetate; (yield=68.9%)

Starting Material: N- [5-(N',N'-dibutylaminosulfonyl)-2-thenoyl)-glycine methyl ester
N.M.R. (CDCl$_3$) δppm: 0.86 (t, 6H, J=7.32 Hz); 1.33~1.37 (m, 4H); 1.40~1.48 (m, 4H); 2.04 (t, 4H, J=7.32 Hz); 3.71 (s, 3H); 5.23 (s, 2H); 7.22 (d, 1H, J=5.25 Hz); 7.67 (d, 1H, J=5.25 Hz).
I.R. νNaCl (cm$^{-1}$): 2950, 1760, 1360, 1220, 1150.
Mass: m/z 415 [M+]

(3-16) methyl
[5-(5-piperidinosulfonyl-2-thienyl)tetrazol-1-yl] acetate;
(yield=45.9%)

Starting Material: N-(5-piperidinosulfonyl-2-thenoyl)glycine methyl ester
M.P.: 133-135° C.

N.M.R. (CDCl$_3$) δppm: 1.04~1.53 (m, 2H); 1.59~1.68 (m, 4H); 2.92 (t, 4H, J=5.25 Hz); 3.71 (s, 3H); 5.23 (s, 2H); 7.26 (d, 1H, J=5.13 Hz); 7.72 (d, 1H, J=5.13 Hz).

I.R. νKBr (cm$^{-1}$): 3100, 2950, 1760, 1340, 1220, 1150, 940, 710, 590.

Mass m/z 371 [M+](3-17) methyl [5- [2-(N,N-diethylaminosulfonyl)-5-trimethylsilyl-3-thienyl] tetrazol-1-yl] acetate; (yield=75.4%)

Starting Material: N- [2-(N',N'-diethylaminosulfonyl)-5-trimethylsilyl-3-thenoyl] glycine methyl ester N.M.R. (CDCl$_3$) δppm: 0.37 (s, 9H); 1.08 (t, 6H, J=7.20 Hz); 3.06 (g, 4H, J=7.08 Hz); 3.71 (s, 3H); 5.21 (s, 2H); 7.24 (s, 1H).

I.R. νNaCl (cm$^{-1}$): 2950, 1760, 1440, 1350, 1250, 1220, 1140, 1000, 840, 700.

Mass m/z 431 [M+]

(3-18) methyl [5-(3-hydroxy-2-thienyl)tetrazol-1-yl] acetate (yield=54.0%)

Starting Material: N-(3-hydroxy-2 thenoyl)glycine methyl ester
M.P.=141-142° C.

N.M.R. (CDCl$_3$) δppm: 3.84 (s, 3H); 5.38 (s, 2H); 6.95 (d, 1H, J=5.37 Hz); 7.46 (d, 1H, J=5.37 Hz); 10.12 (bs, 1H).

I.R. νKBr (cm$^{-1}$): 3100, 1760, 1740, 1530, 1220, 1000.
Mass: m/z 240 [M+]

The compounds prepared in the foregoing Examples are listed in the folowing Table I.

TABLE I

| Ex. No. | R$_1$ | R$_2$ | X |
|---|---|---|---|
| 1-1 | —CH$_3$ | H | S (2)*$^2$ |
| 1-2 | —CH$_3$ | —CH$_3$ (3)*$^1$ | S (2) |
| 1-3 | —CH$_3$ | —CH$_3$ (4) | S (2) |
| 1-4 | —CH$_3$ | —CH$_3$ (5) | S (2) |
| 1-5 | —CH$_3$ | H | S (3) |
| 1-6 | —CH$_3$ | H | O (2) |
| 1-7 | —CH$_3$ | H | O (3) |
| 1-8 | —CH$_3$ | —CH$_2$CH$_3$ (5) | S (2) |
| 1-9 | —CH$_3$ | —CH$_2$—ph (5) | S (2) |
| 1-10 | —CH$_3$ | —SCH$_3$ 5) | S (2) |
| 1-11 | —CH$_3$ | —Br (5) | S (2) |
| 1-12 | —CH$_3$ | —CH$_3$ (2) | S (3) |
| 1-13 | —CH$_3$ | —CH$_2$Br (5) | S (2) |
| 1-14 | —CH$_3$ | —ph (5) | S (2) |
| 1-15 | —CH$_3$ | —NHCOCH$_3$ (3) | S (2) |
| 1-16 | —CH$_3$ | —NHCOCH$_2$CH$_2$CH$_3$ (3) | S (2) |
| 1-17 | —CH$_3$ | —NHCOCH$_2$CH$_2$—ph (3) | S (2) |
| 1-18 | —CH$_3$ | —CH$_3$ (5) | O (2) |
| 1-19 | —CH$_3$ | —CH$_2$CH$_2$CH$_2$CH$_3$ (5) | O (2) |
| 1-20 | —CH$_3$ | —Br (5) | O (2) |
| 1-21 | —CH$_3$ | —SCH$_3$ (5) | O (2) |
| 1-22 | —CH$_3$ | —Br (2) | O (3) |
| 1-23 | —CH$_3$ | —CH(n-C$_3$H$_7$)—CH$_2$CH$_2$CH$_2$CH$_3$ (2) | O (3) |
| 1-24 | —CH$_3$ | —SCH$_3$ (2) | O (3) |
| 1-25 | —CH$_3$ | —NHSO$_2$CH$_3$ (3) | S (2) |
| 1-26 | —CH$_3$ | —NHSO$_2$CH$_2$CH$_2$CH$_2$CH$_3$ (3) | S (2) |
| 1-27 | —CH$_3$ | —NHSO$_2$—ph (3) | S (2) |
| 1-28 | —CH$_3$ | —CH$_3$ (2) | O (3) |
| 1-29 | —CH$_3$ | —SO$_2$N(CH$_3$)—CH$_2$CH$_2$OCH$_2$OCH$_3$ (5) | S (2) |
| 2-1 | —H | H | S (2) |
| 2-2 | —H | —CH$_3$ (3) | S (2) |
| 2-3 | —H | —CH$_3$ (4) | S (2) |
| 2-4 | —H | —CH$_3$ (5) | S (2) |
| 2-5 | —H | H | S (3) |
| 2-6 | —H | H | O (2) |
| 2-7 | —H | H | O (3) |
| 2-8 | —H | —C$_2$H$_5$ (5) | S (2) |
| 2-9 | —H | —CH$_2$—ph (5) | S (2) |
| 2-10 | —H | —SCH$_3$ (5) | S (2) |
| 2-11 | —H | —Br (5) | S (2) |
| 2-12 | —H | —CH$_3$ (2) | S (3) |
| 2-13 | —H | —CH$_2$Br (5) | S (2) |
| 2-14 | —H | —ph (5) | S (2) |
| 2-15 | —H | —OCH$_3$ (3) | S (2) |
| 2-16 | —H | —OCH$_2$CH$_2$CH$_3$ (3) | S (2) |
| 2-17 | —H | —NHCOCH$_3$ (3) | S (2) |
| 2-18 | —H | —NHCOCH$_2$CH$_3$ (3) | S (2) |
| 2-19 | —H | —NHCOCH$_2$CH$_2$—ph (3) | S (2) |
| 2-20 | —H | —CH$_2$CH$_2$CH$_2$CH$_3$ (5) | S (2) |
| 2-21 | —H | —CH$_2$CH$_2$CH$_2$—ph (5) | S (2) |
| 2-22 | —H | —CH$_2$OCH$_3$ (5) | S (2) |
| 2-23 | —H | —CH$_2$OCH$_2$CH$_2$CH$_2$CH$_3$ (5) | S (2) |
| 2-24 | —H | —Br (2) | S (3) |
| 2-25 | —H | —CH(n-C$_3$H$_7$)—CH$_2$CH$_2$CH$_2$CH$_3$ (2) | S (3) |
| 2-26 | —H | —SCH$_3$ (2) | S (3) |
| 2-27 | —H | —CH$_3$ (5) | O (2) |
| 2-28 | —H | —CH$_2$CH$_2$CH$_2$CH$_3$ (5) | O (2) |

TABLE I-continued

| Ex. No. | R₁ | R₂ | X |
|---|---|---|---|
| 2-29 | —H | —Br (5) | O (2) |
| 2-30 | —H | —SCH₃ (5) | O (2) |
| 2-31 | —H | —Br (2) | O (3) |
| 2-32 | —H | —SCH₃ (2) | O (3) |
| 2-33 | —H | —S—ph (2) | S (3) |
| 2-34 | —H | —S—ph (5) | S (2) |
| 2-35 | —H | —SO₂—N(C₂H₅)₂ (5) | S (2) |
| 2-36 | —H | —SO₂—N(CH₂CH₂CH₂CH₃)₂ (5) | S (2) |
| 2-37 | —H | —SO₂—pip (5) | S (2) |
| 2-38 | —H | —SO₂—N(C₂H₅)₂ (2) | S (3) |
| 2-39 | —H | —NHSO₂CH₃ (3) | S (2) |
| 2-40 | —H | —NHSO₂CH₂CH₂CH₂CH₃ (3) | S (2) |
| 2-41 | —H | —NHSO₂—ph (3) | S (2) |
| 2-42 | —H | —OH (3) | S (2) |
| 2-43 | —H | —SOCH₃ (2) | S (3) |
| 2-44 | —H | —SO₂CH₃ (2) | S (3) |
| 2-45 | —H | —NH₂.HCl (3) | S (2) |
| 2-46 | —H | —SO₂—N(CH₃)—CH₂CH₂OH (5) | S (2) |
| 3-1 | —CH₃ | H | S (2) |
| 3-2 | —C₂H₅ | H | S (3) |
| 3-3 | —CH₃ | —OCH₃ (3) | S (2) |
| 3-4 | —CH₃ | —OCH₂CH₂CH₂CH₃ (3) | S (2) |
| 3-5 | —CH₃ | —CH₂CH₂CH₂CH₃ (5) | S (2) |
| 3-6 | —CH₃ | —CH₂CH₂CH₂—ph (5) | S (2) |
| 3-7 | —CH₃ | —CH₂OCH₃ (5) | S (2) |
| 3-8 | —CH₃ | —CH₂OCH₂CH₂CH₂CH₃ (5) | S (2) |
| 3-9 | —CH₃ | —Br (2) | S (3) |
| 3-10 | —CH₃ | —CH(n-C₃H₇)CH₂CH₂CH₂CH₃ (2) | S (3) |
| 3-11 | —CH₃ | —SCH₃ (2) | S (3) |
| 3-12 | —CH₃ | —S—ph (2) | S (3) |
| 3-13 | —CH₃ | —S—ph (5) | S (2) |
| 3-14 | —CH₃ | —SO₂—N(C₂H₅)₂ (5) | S (2) |
| 3-15 | —CH₃ | —SO₂—N(n-C₄H₅)₂ (5) | S (2) |
| 3-16 | —CH₃ | —SO₂—pip (5) | S (2) |
| 3-17 | —CH₃ | —SO₂—N(C₂H₅)₂ (2) —Si(CH₃)₃ (5) | S (3) |
| 3-18 | H | —OH (3) | S (2) |

In Table I, "—ph" and "—pip" mean a phenyl and piperidino groups respectively.

*¹Each numeral given in parentheses means the position on the thiophene or furan ring at which each substituent is bonded.

*²Each numeral given in parentheses means the position on the thiophene or furan ring at which the tetrazolyl group is bonded at its 5-position.

thiophene or furan ring at which the tetrazolyl group is bonded at its 5-position.

As has been explained above in detail, the aldose reductase inhibitor of the present invention shows excellent aldose reductase inhibitory effect and has low toxicity. Therefore, it can be used as a medicine for preventing and/or treating mammalian inclusive of man suffering from diabetic complications such as neural disorders, nephrosis, cataract and retinopathy with safety.

The effects and toxicity of the aldose reductase inhibitor according to the present invention will be detailed below with reference to the following Test Examples.

TEST EXAMPLE 1: TEST FOR EXAMINING ALDOSE REDUCTASE INHIBITORY EFFECT (i) Methodology Six-weeks-old male SD rats were anesthetized with ether and killed. Then their crystalline lenses were immediately removed and stored at $-80°$ C. The lenses were homogenized in 3 volumes of 135 mM sodium potassium phosphate buffer (pH 7.0) and centrifuged at 30,000 rpm for 30 minutes. The resulting supernatant was dialyzed overnight against 0.05 M sodium chloride solution to obtain an aldose reductase solution. All operations were conducted at 4° C. and the enzyme solution was stored at $-80°$ C.

The activity of aldose reductase was determined according to a partially modified method of J.H. Kinoshita et al (J. Biol. Chem., 1965, 240, p. 877). More specifically, 0.1 ml of DL glyceraldehyde (final concentration: 10 mM) was added to 0.9 ml of 100 mM sodium potassium phosphate buffer (pH 6.2) which contained lithium sulfate (final concentration: 400 mM), reduced nicotinamide adenine dinucleotide phosphate (final concentration: 0.15 mM), the enzyme solution, and the compound to be evaluated (final concentration: $10^{-6}$ M, $10^{-7}$ M or $10^{-8}$ M), and then the reaction was conducted at 30° C. for 5 minutes. During the reaction, the change in the absorbance at 340 nm with time was monitored. The maximum reducing rate of the absorbance (U) during the reaction was determined. By subtracting, from this value, the maximum reducing rate ($U_o$) at 340 nm of the reaction solution before the addition of the substrate (DL-glyceraldehyde), the reaction rate ($V = U - U_o$) was calculated as a true reaction rate in the presence of the compound to be tested.

The same procedure was repeated except for the absence of the compound to be tested. A true reaction rate ($V_o$) in case the enzyme was not inhibited was calculated ($V_o = U' - U_o'$). The aldose reductase inhibitory activity of the test compounds was determined according to the following formula:

*Rate of Inhibition* $(\%) = (V_o - V)/V_o \times 100$

For comparison, the same tests were conducted using a known aldose reductase inhibitor: ONO-2235 [(E)-3-carboxymethyl-5- [(2E)-methyl-3-phenylpropenylidene] rhodan].

(ii) Results

The results thus obtained are summarized in the following Table II. As seen from Table II, the compounds of the present invention tested show aldose reductase inhibitory effect identical to or superior to those attained by the known inhibitor ONO-2235.

TABLE II

| Compound Tested (Ex. No.) | IC$_{50}$ ($10^{-8}$) M |
|---|---|
| 1-5 | 95 |
| 1-7 | 74 |
| 1-27 | 23 |
| 2-1 | 1.6 |
| 2-2 | 1.8 |
| 2-3 | 2.4 |
| 2-4 | 2.3 |
| 2-5 | 2.1 |
| 2-6 | 6.0 |
| 2-7 | 3.0 |
| 2-8 | 2.1 |
| 2-9 | 2.0 |
| 2-10 | 2.0 |
| 2-11 | 1.9 |
| 2-12 | 3.0 |
| 2-13 | 2.5 |
| 2-14 | 2.1 |
| 2-15 | 2.9 |
| 2-16 | 3.1 |
| 2-17 | 2.8 |
| 2-18 | 2.0 |
| 2-19 | 2.4 |
| 2-20 | 2.3 |
| 2-21 | 2.8 |
| 2-22 | 3.1 |
| 2-23 | 2.5 |
| 2-24 | 3.8 |
| 2-26 | 3.1 |
| 2-27 | 15 |
| 2-28 | 13 |
| 2-29 | 16 |
| 2-30 | 11 |
| 2-31 | 8.5 |
| 2-32 | 3.5 |
| 2-33 | 2.4 |
| 2-34 | 2.6 |
| 2-35 | 39 |
| 2-36 | 8.5 |
| 2-37 | 23 |
| 2-38 | 46 |
| 2-39 | 2.8 |
| 2-40 | 1.6 |
| 2-41 | 2.3 |
| 2-42 | 2.0 |
| 2-43 | 30 |
| 2-44 | 52 |
| 3-2 | 58 |
| 3-5 | 18 |
| 3-11 | 38 |
| ONO-2235 | 2.2 |

TEST EXAMPLE 2: TEST ON THE EFFECT OF INHIBITING THE ACCUMULATION OF SORBITOL IN SCIATIC NERVE (i) Methodology Groups of 6 to 8-weeks-old Sprague-Dawley male rats (4 animals per group) were fasted for 18 hours and streptozotocin was injected through the tail vein in a dose of 60 mg/kg to thus obtain diabetic rats. Immediately after the administration of the streptozotocin, each compound to be tested was orally administered to these rats in the form of a suspension at a dose of 10 mg/kg, 30 mg/kg and 50 mg/kg (each was suspended in a 0.5% sodium carboxymethyl cellulose solution) twice a day (9 o'clock in the morning and 5 o'clock in the afternoon) for 5 days. During the test, the rats took diet and drank water freely. 4 Hours after the final administration of the drug in the 5th day's morning (9 o'clock in the morning), the rats were sacrificed and then the sciatic nerve thereof was removed to determine the amount of sorbitol accumulated therein.

The results are expressed in the percentage obtained while the value obtained on the control to which any drug was not administered is defined to be 100.

(ii) Test Results

The results of the test are listed in the following Table III. These results indicate that the compounds of the present invention show high inhibitory effect as compared with those for the known aldose reductase inhibitor ONO-2235.

TABLE III

| Compound Tested (Ex. No.) | Rate of Inhibition of Sorbitol Accumulation (%) | | |
|---|---|---|---|
| | 10 mg/kg | 30 mg/kg | 50 mg/kg |
| 2-1 | 68 | 89 | — |
| 2-2 | 62 | 93 | — |
| 2-5 | 73 | 90 | — |
| 2-7 | 46 | 77 | — |
| ONO-2235 | 0 | 0 | 40 |

TEST EXAMPLE 3: ACUTE TOXICITY TEST (i) Methodology

Each compound to be tested was suspended to 0.5% sodium carboxymethyl cellulose solution and the resulting suspension was orally administered to 6-weeks-old male MCH mice (5 animals per test group). The 50% lethal dose (LD$_{50}$; mg/kg) was evaluated from the mortality rate (%) observed 14 days after the administration of the compound. The mice took diet and drank water freely during the test.

(ii) Results

The results obtained are summarized in the following Table IV. As seen from Table IV, the compounds of the present invention which were subjected to the foregoing test show LD$_{50}$ of not less than 3,000 mg/kg.

TABLE IV

| Compound Tested (Ex. No.) | LD$_{50}$ (mg/kg) |
|---|---|
| 2-1 | >3,000 |
| 2-5 | >3,000 |
| 2-7 | >3,000 |

What is claimed is:

1. A tetrazoleacetic acid derivative represented by the following general formula (I):

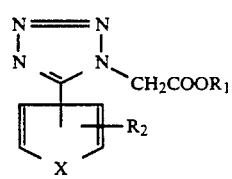

[in Formula (I), R$_1$ represents a hydrogen atom or an alkyl group; R$_2$ represents a hydrogen atom, an alkyl group, an aralkyl group, a halogen atom, a haloalkyl group, a hydroxyl group, an alkoxy group, an alkoxyalkyl group, an amino group, an aryl group, an alkyl or aryl thio group, an alkyl or aryl carbonylamino group, an alkyl or aryl sulfonylamino group, an alkyl or aryl aminosulfonyl group, an alkyl or aryl sulfonyl group or an alkyl or aryl sulfinyl group; and X represents —O— or —S—] except for [5-(2-thienyl)tetrazol-1-yl] acetic acid, [5-(2-furyl)tetrazol-1-yl] acetic acid and ethyl esters thereof, or a salt thereof.

2. The tetrazoleacetic acid derivative of claim 1 wherein, in the general formula (I), the alkyl group represented by $R_1$ or $R_2$ is selected from the group consisting of methyl, ethyl, propyl, isopropyl, butyl, isobutyl and t-butyl groups, the aralkyl group is a benzyl or phenylpropyl group; the alkoxy group is a member selected from the group consisting of methoxy, ethoxy, propoxy, isopropoxy, butoxy, isobutoxy and t-butoxy groups, the alkoxyalkyl group is a methoxymethyl or butoxymethyl group; the haloalkyl group is a mono-, di- or tri-haloalkyl group; the alkyl or aryl thio group is a member selected from the group consisting of methylthio, ethylthio, butylthio and phenylthio groups; the alkylaminosulfonyl group is a mono- or di-alkylaminosulfonyl group; the alkyl or aryl sulfonylamino group is a member selected from the group consisting of methylsulfonylamino, ethylsulfonylamino, butylsulfonylamino and phenylsulfonylamino groups; the alkyl or aryl carbonylamino group is a member selected from the group consisting of methylcarbonylamino, ethylcarbonylamino, propylcarbonylamino and phenethylcarbonylamino groups; the alkyl or aryl sulfonyl group is a member selected from the group consisting of methylsulfonyl, ethylsulfonyl, butylsulfonyl and piperidinosulfonyl groups; and the alkylsulfinyl group is a member selected from the group consisting of methylsulfinyl, ethylsulfinyl and butylsulfinyl groups.

3. The tetrazoleacetic acid derivative of claim 2 wherein the haloalkyl group is a member selected from the group consisting of chloromethyl, bromomethyl, fluoromethyl and chlorobutyl groups; and the alkylaminosulfonyl group is a member selected from the group consisting of methylaminosulfonyl, ethylaminosulfonyl, propylaminosulfonyl and butylaminosulfonyl groups.

4. The tetrazoleacetic acid derivative of claim 1 wherein the salt of the compound represented by Formula (I) wherein $R_1$ is a hydrogen atom is a member selected from the group consisting of alkali metal salts, alkaline earth metal salts, ammonium salts, organic amine salts and salts with basic amino acids.

5. The tetrazoleacetic acid derivative of claim 4 wherein the alkali metal salt is a sodium salt or a potassium salt; the alkaline earth metal salt is a calcium salt or a magnesium salt; the organic amine salt is a triethylamine salt, a pyridine salt or an ethanolamine salt; and the basic amino acid salt is an arginine salt.

6. The tetrazoleacetic acid derivative of claim 1 wherein, in the foregoing Formula (I), $R_1$ is a hydrogen atom and X is an oxygen or sulfur atom.

7. An aldose reductase inhibitor comprising a tetrazoleacetic acid derivative represented by the following general formula (II):

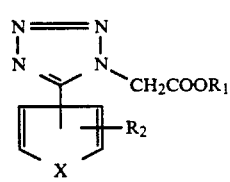

[in Formula (II), $R_1$ represents a hydrogen atom or an alkyl group; $R_2$ represents a hydrogen atom, an alkyl group, an aralkyl group, a halogen atom, a haloalkyl group, a hydroxyl group, an alkoxy group, an alkoxyalkyl group, an amino group, an aryl group, an alkyl or aryl thio group, an alkyl or aryl carbonylamino group, an alkyl or aryl sulfonylamino group, an alkyl or aryl aminosulfonyl group, an alkyl or aryl sulfonyl group or an alkyl or aryl sulfinyl group; and X represents —O— or —S—] or a salt thereof and a pharmaceutically acceptable carrier.

8. The aldose reductase inhibitor of claim 7 wherein, in the general formula (II), the lower alkyl group represented by $R_1$ or $R_2$ is selected from the group consisting of methyl, ethyl, propyl, isopropyl, butyl, isobutyl and t-butyl groups; the aralkyl group is a benzyl or phenylpropyl group; the alkoxy group is a member selected from the group consisting of methoxy, ethoxy, propoxy, isopropoxy, butoxy, isobutoxy and t-butoxy groups; the alkoxyalkyl group is a methoxymethyl or butoxymethyl group; the haloalkyl group is a mono-, di- or tri-haloalkyl group; the alkyl or aryl thio group is a member selected from the group consisting of methylthio, ethylthio, butylthio and phenylthio groups; the alkylaminosulfonyl group is a mono- or di-alkylaminosulfonyl group; the alkyl or aryl sulfonylamino group is a member selected from the group consisting of methylsulfonylamino, ethylsulfonylamino, butylsulfonylamino and phenylsulfonylamino groups; the alkyl or aryl carbonylamino group is a member selected from the group consisting of methylcarbonylamino, ethylcarbonylamino, propylcarbonylamino and phenethylcarbonylamino groups; the alkyl or aryl sulfonyl group is a member selected from the group consisting of methylsulfonyl, ethylsulfonyl, butylsulfonyl and piperidinosulfonyl groups; and the alkylsulfinyl group is a member selected from the group consisting of methylsulfinyl, ethylsulfinyl and butylsulfinyl groups.

9. The aldose reductase inhibitor of claim 8 wherein the haloalkyl group is a member selected from the group consisting of chloromethyl, bromomethyl, fluoromethyl and chlorobutyl groups; and the alkylaminosulfonyl group is a member selected from the group consisting of methylaminosulfonyl, ethylaminosulfonyl, propylaminosulfonyl and butylaminosulfonyl groups.

10. The aldose reductase inhibitor of claim 7 wherein the salt of the compound represented by Formula (II) wherein $R_1$ is a hydrogen atom is a member selected from the group consisting of alkali metal salts, alkaline earth metal salts, ammonium salts, organic amine salts and salts with basic amino acids.

11. The aldose reductase inhibitor of claim 10 wherein the alkali metal salt is a sodium salt or a potassium salt; the alkaline earth metal salt is a calcium salt or a magnesium salt; the organic amine salt is a triethylamine salt, a pyridine salt or an ethanolamine salt; and the basic amino acid salt is an arginine salt.

12. The aldose reductase inhibitor of claim 7 wherein, in Formula (II), $R_1$ is a hydrogen atom and X is an oxygen or sulfur atom.

13. A method for alleviating or reducing diabetic complications wherein a tetrazoleacetic acid derivative represented by the following general formula (II):

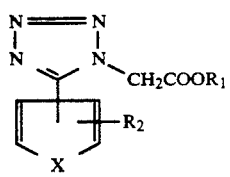

(II)

[in Formula (II), $R_1$ represents a hydrogen atom or an alkyl group; $R_2$ represents a hydrogen atom, an alkyl group, an aralkyl group, a halogen atom, a haloalkyl group, a hydroxyl group, an alkoxy group, an alkoxyalkyl group, an amino group, an aryl group, an alkyl or aryl thio group, an alkyl or aryl carbonylamino group, an alkyl or aryl sulfonylamino group, an alkyl or aryl aminosulfonyl group, an alkyl or aryl sulfonyl group or an alkyl or aryl sulfinyl group; and X represents —O— or —S—] or a salt thereof is used.

14. The method of claim 13 wherein, in the general formula (II), the alkyl group represented by $R_1$ or $R_2$ is selected from the group consisting of methyl, ethyl, propyl, isopropyl, butyl, isobutyl and t-butyl groups; the aralkyl group is a benzyl or phenylpropyl group; the alkoxy group is a member selected from the group consisting of methoxy, ethoxy, propoxy, isopropoxy, butoxy, isobutoxy and t-butoxy groups; the alkoxyalkyl group is a methoxymethyl or butoxymethyl group; the haloalkyl group is a mono-, di- or tri-haloalkyl group; the alkyl or aryl thio group is a member selected from the group consisting of methylthio, ethylthio, butylthio and phenylthio groups; the alkylaminosulfonyl group is a mono- or di-alkylaminosulfonyl group; the alkyl or aryl sulfonylamino group is a member selected from the group consisting of methylsulfonylamino, ethylsulfonylamino, butylsulfonylamino and phenylsulfonylamino groups; the alkyl or aryl carbonylamino group is a member selected from the group consisting of methylcarbonylamino, ethylcarbonylamino, propylcarbonylamino and phenethylcarbonylamino groups; the alkyl or aryl sulfonyl group is a member selected from the group consisting of methylsulfonyl, ethylsulfonyl, butylsulfonyl and piperidinosulfonyl groups; and the alkylsulfinyl group is a member selected from the group consisting of methylsulfinyl, ethylsulfinyl and butylsulfinyl groups.

15. The method of claim 14 wherein the haloalkyl group is a member selected from the group consisting of chloromethyl, bromomethyl, fluoromethyl and chlorobutyl groups; and the alkylaminosulfonyl group is a member selected from the group consisting of methylaminosulfonyl, ethylaminosulfonyl, propylaminosulfonyl and butylaminosulfonyl groups.

16. The method of claim 13 wherein the salt of the compound represented by Formula (II) wherein $R_1$ is a hydrogen atom is a member selected from the group consisting of alkali metal salts, alkaline earth metal salts, ammonium salts, organic amine salts and salts with basic amino acids.

17. The method of claim 16 wherein the alkali metal salt is a sodium salt or a potassium salt; the alkaline earth metal salt is a calcium salt or a magnesium salt; the organic amine salt is a triethylamine salt, a pyridine salt or an ethanolamine salt; and the basic amino acid salt is an arginine salt.

18. The method of claim 13 wherein, in Formula (II), $R_1$ is a hydrogen atom and X is an oxygen or sulfur atom.

19. The method of claim 13 wherein the compound is administered, at one time or over several times, in an amount ranging from 1 to 1,000 mg per day for adult, orally, subcutaneously, intravenously or locally.

20. The method of claim 13 wherein the compound is administered in the form of tablets, powder, fine particles, granules, capsules, pills, liquid preparations, solutions or suspensions for injection or eye drops.

* * * * *